(12) United States Patent
Field et al.

(10) Patent No.: US 11,950,879 B2
(45) Date of Patent: Apr. 9, 2024

(54) ESTIMATION OF SOURCE-DETECTOR SEPARATION IN AN OPTICAL MEASUREMENT SYSTEM

(71) Applicant: HI LLC, Los Angeles, CA (US)

(72) Inventors: Ryan Field, Culver City, CA (US); Katherine Perdue, Los Angeles, CA (US); Hamid Dehghani, Birmingham (GB)

(73) Assignee: HI LLC, Los Angeles, CA (US)

(*) Notice: Subject to any disclaimer, the term of this patent is extended or adjusted under 35 U.S.C. 154(b) by 290 days.

(21) Appl. No.: 17/176,448

(22) Filed: Feb. 16, 2021

(65) Prior Publication Data

US 2021/0259554 A1    Aug. 26, 2021

Related U.S. Application Data

(60) Provisional application No. 63/071,473, filed on Aug. 28, 2020, provisional application No. 62/992,543, (Continued)

(51) Int. Cl.
*A61B 5/00* (2006.01)
*G01B 11/14* (2006.01)

(52) U.S. Cl.
CPC .......... *A61B 5/0082* (2013.01); *A61B 5/4064* (2013.01); *A61B 5/6803* (2013.01); (Continued)

(58) Field of Classification Search
None
See application file for complete search history.

(56) References Cited

U.S. PATENT DOCUMENTS

| 4,018,534 A | 4/1977 | Thorn et al. |
| 4,207,892 A | 6/1980 | Binder |

(Continued)

FOREIGN PATENT DOCUMENTS

| CN | 200950235 | 9/2007 |
| CN | 107865635 | 4/2018 |

(Continued)

OTHER PUBLICATIONS

Alayed, et al.,"Characterization of a Time-Resolved Diffuse Optical Spectroscopy Prototype Using Low-Cost, Compact Single Photon Avalanche Detectors for Tissue Optics Applications," Sensors 2018, 18, 3680; doi:10.3390/s18113680.

(Continued)

*Primary Examiner* — Jennifer D Bennett
*Assistant Examiner* — Erin R Garber
(74) *Attorney, Agent, or Firm* — ALG Intellectual Property, LLC

(57) ABSTRACT

An optical measurement system includes a first light source configured to emit a first light pulse toward a target, a second light source configured to emit a second light pulse toward the target, a first detector, a second detector, and a processing unit. The processing unit is configured to determine a plurality of temporal distributions of photons included in the first light pulse and the second light pulse and detected by the first detector and the second detector after the photons are scattered by the target. The processing unit is further configured to determine, based on the plurality of temporal distributions, a distance between the first light source and the second detector.

27 Claims, 23 Drawing Sheets

Related U.S. Application Data filed on Mar. 20, 2020, provisional application No. 62/979,866, filed on Feb. 21, 2020.

(52) U.S. Cl.
CPC ...... *G01B 11/14* (2013.01); *A61B 2562/0238* (2013.01); *A61B 2576/026* (2013.01)

(56) References Cited

U.S. PATENT DOCUMENTS

| | | | |
|---|---|---|---|
| 4,281,645 | A | 8/1981 | Jobsis |
| 4,321,930 | A | 3/1982 | Jobsis |
| 4,515,165 | A | 5/1985 | Carroll |
| 4,655,225 | A | 4/1987 | Dahne et al. |
| 4,928,248 | A | 5/1990 | Takahashi et al. |
| 4,963,727 | A | 10/1990 | Cova |
| 4,995,044 | A | 2/1991 | Blazo |
| 5,088,493 | A | 2/1992 | Giannini |
| 5,090,415 | A | 2/1992 | Yamashita |
| 5,218,962 | A | 6/1993 | Mannheimer et al. |
| 5,309,458 | A | 5/1994 | Carl |
| 5,386,827 | A | 2/1995 | Chance et al. |
| 5,528,365 | A | 6/1996 | Gonatas et al. |
| 5,625,458 | A | 4/1997 | Alfano et al. |
| 5,761,230 | A | 6/1998 | Oono et al. |
| 5,853,370 | A | 12/1998 | Chance et al. |
| 5,895,984 | A | 4/1999 | Renz |
| 5,929,982 | A | 7/1999 | Anderson |
| 5,983,120 | A | 11/1999 | Groner et al. |
| 5,987,045 | A | 11/1999 | Albares et al. |
| 6,163,715 | A | 12/2000 | Larsen et al. |
| 6,240,309 | B1 | 5/2001 | Yamashita et al. |
| 6,291,824 | B1 * | 9/2001 | Battarbee ............ A61B 5/0073 250/341.7 |
| 6,384,663 | B2 | 5/2002 | Cova et al. |
| 6,541,752 | B2 | 4/2003 | Zappa et al. |
| 6,542,763 | B1 | 4/2003 | Yamashita et al. |
| 6,618,614 | B1 | 9/2003 | Chance |
| 6,640,133 | B2 | 10/2003 | Yamashita |
| 6,683,294 | B1 | 1/2004 | Herbert et al. |
| 6,748,254 | B2 | 6/2004 | O'Neil |
| 6,992,772 | B2 | 1/2006 | Block |
| 7,095,491 | B2 | 8/2006 | Forstner et al. |
| 7,356,365 | B2 | 4/2008 | Schurman |
| 7,507,596 | B2 | 3/2009 | Yaung et al. |
| 7,547,872 | B2 | 6/2009 | Niclass et al. |
| 7,613,504 | B2 | 11/2009 | Rowe |
| 7,667,400 | B1 | 2/2010 | Goushcha |
| 7,705,284 | B2 | 4/2010 | Inoue et al. |
| 7,714,292 | B2 | 5/2010 | Agarwal et al. |
| 7,774,047 | B2 | 8/2010 | Yamashita et al. |
| 7,899,506 | B2 | 3/2011 | Xu et al. |
| 8,026,471 | B2 | 9/2011 | Itzler |
| 8,078,250 | B2 | 12/2011 | Chen et al. |
| 8,082,015 | B2 | 12/2011 | Yodh et al. |
| 8,115,170 | B2 | 2/2012 | Stellari et al. |
| 8,168,934 | B2 | 5/2012 | Niclass et al. |
| 8,352,012 | B2 | 1/2013 | Besio |
| 8,633,431 | B2 | 1/2014 | Kim |
| 8,637,875 | B2 | 1/2014 | Finkelstein et al. |
| 8,754,378 | B2 | 6/2014 | Prescher et al. |
| 8,817,257 | B2 | 8/2014 | Herve |
| 8,937,509 | B2 | 1/2015 | Xu et al. |
| 8,986,207 | B2 | 3/2015 | Li |
| 9,012,860 | B2 | 4/2015 | Nyman et al. |
| 9,041,136 | B2 | 5/2015 | Chia |
| 9,058,081 | B2 | 6/2015 | Baxter |
| 9,076,707 | B2 | 7/2015 | Harmon |
| 9,101,279 | B2 | 8/2015 | Ritchey et al. |
| 9,131,861 | B2 | 9/2015 | Ince et al. |
| 9,157,858 | B2 | 10/2015 | Claps |
| 9,160,949 | B2 | 10/2015 | Zhang et al. |
| 9,176,241 | B2 | 11/2015 | Frach |
| 9,178,100 | B2 | 11/2015 | Webster et al. |
| 9,190,552 | B2 | 11/2015 | Brunel et al. |
| 9,201,138 | B2 | 12/2015 | Eisele et al. |
| 9,209,320 | B1 | 12/2015 | Webster |
| 9,257,523 | B2 | 2/2016 | Schneider et al. |
| 9,257,589 | B2 | 2/2016 | Niclass et al. |
| 9,299,732 | B2 | 3/2016 | Webster et al. |
| 9,299,873 | B2 | 3/2016 | Mazzillo et al. |
| 9,312,401 | B2 | 4/2016 | Webster |
| 9,316,735 | B2 | 4/2016 | Baxter |
| 9,331,116 | B2 | 5/2016 | Webster |
| 9,368,487 | B1 | 6/2016 | Su et al. |
| 9,401,448 | B2 | 7/2016 | Bienfang et al. |
| 9,407,796 | B2 | 8/2016 | Dinten et al. |
| 9,419,635 | B2 | 8/2016 | Kumar et al. |
| 9,431,439 | B2 | 8/2016 | Soga et al. |
| 9,442,201 | B2 | 9/2016 | Schmand et al. |
| 9,449,377 | B2 | 9/2016 | Sarkar et al. |
| 9,450,007 | B1 | 9/2016 | Motta et al. |
| 9,466,631 | B2 | 10/2016 | Fallica et al. |
| 9,476,979 | B2 | 10/2016 | Drader et al. |
| 9,478,579 | B2 | 10/2016 | Dai et al. |
| 9,529,079 | B1 | 12/2016 | Droz |
| 9,535,157 | B2 | 1/2017 | Caley et al. |
| 9,574,936 | B2 | 2/2017 | Heinonen |
| 9,625,580 | B2 | 4/2017 | Kotelnikov et al. |
| 9,627,569 | B2 | 4/2017 | Harmon |
| 9,634,826 | B1 | 4/2017 | Park |
| 9,639,063 | B2 | 5/2017 | Dutton et al. |
| 9,640,704 | B2 | 5/2017 | Frey et al. |
| 9,658,158 | B2 | 5/2017 | Renna et al. |
| 9,659,980 | B2 | 5/2017 | McGarvey et al. |
| 9,671,284 | B1 | 6/2017 | Dandin |
| 9,681,844 | B2 | 6/2017 | Xu et al. |
| 9,685,576 | B2 | 6/2017 | Webster |
| 9,702,758 | B2 | 7/2017 | Nouri |
| 9,728,659 | B2 | 8/2017 | Hirigoyen et al. |
| 9,741,879 | B2 | 8/2017 | Frey et al. |
| 9,753,351 | B2 | 9/2017 | Eldada |
| 9,767,246 | B2 | 9/2017 | Dolinsky et al. |
| 9,768,211 | B2 | 9/2017 | Harmon |
| 9,773,930 | B2 | 9/2017 | Motta et al. |
| 9,804,092 | B2 | 10/2017 | Zeng et al. |
| 9,812,438 | B2 | 11/2017 | Schneider et al. |
| 9,831,283 | B2 | 11/2017 | Shepard et al. |
| 9,851,302 | B2 | 12/2017 | Mattioli Della Rocca et al. |
| 9,867,250 | B1 | 1/2018 | Powers et al. |
| 9,869,753 | B2 | 1/2018 | Eldada |
| 9,881,963 | B1 | 1/2018 | Chen et al. |
| 9,882,003 | B1 | 1/2018 | Aharoni |
| 9,886,095 | B2 | 2/2018 | Pothier |
| 9,899,544 | B1 | 2/2018 | Mazzillo et al. |
| 9,899,557 | B2 | 2/2018 | Muscara' et al. |
| 9,939,316 | B2 | 4/2018 | Scott et al. |
| 9,939,536 | B2 | 4/2018 | O'Neill et al. |
| 9,946,344 | B2 | 4/2018 | Ayaz et al. |
| D817,553 | S | 5/2018 | Aaskov et al. |
| 9,983,670 | B2 | 5/2018 | Coleman |
| 9,997,551 | B2 | 6/2018 | Mandai et al. |
| 10,016,137 | B1 | 7/2018 | Yang et al. |
| D825,112 | S | 8/2018 | Saez |
| 10,056,415 | B2 | 8/2018 | Na et al. |
| 10,103,513 | B1 | 10/2018 | Zhang et al. |
| 10,141,458 | B2 | 11/2018 | Zhang et al. |
| 10,154,815 | B2 | 12/2018 | Al-Ali et al. |
| 10,157,954 | B2 | 12/2018 | Na et al. |
| 10,158,038 | B1 * | 12/2018 | Do Valle ............... G01S 7/4863 |
| 10,219,700 | B1 | 3/2019 | Yang et al. |
| 10,256,264 | B2 | 4/2019 | Na et al. |
| 10,340,408 | B1 | 7/2019 | Katnani |
| 10,424,683 | B1 | 9/2019 | Do Valle |
| 10,483,125 | B2 | 11/2019 | Inoue |
| 10,515,993 | B2 | 12/2019 | Field et al. |
| 10,533,893 | B2 | 1/2020 | Leonardo |
| 10,541,660 | B2 | 1/2020 | McKisson |
| 10,558,171 | B2 | 2/2020 | Kondo |
| 10,594,306 | B2 | 3/2020 | Dandin |
| 10,627,460 | B2 | 4/2020 | Alford et al. |
| 10,695,167 | B2 | 6/2020 | Van Heugten et al. |
| 10,697,829 | B2 | 6/2020 | Delic |
| 10,772,561 | B2 | 9/2020 | Donaldson |

(56) References Cited

U.S. PATENT DOCUMENTS

| | | | |
|---|---|---|---|
| 10,809,796 B2 | 10/2020 | Armstrong-Muntner | |
| 10,825,847 B2 | 11/2020 | Furukawa | |
| 10,912,504 B2 | 2/2021 | Nakaji | |
| 10,976,386 B2 | 4/2021 | Alford | |
| 10,983,177 B2 | 4/2021 | Jiménez-Martínez | |
| 10,996,293 B2 | 5/2021 | Mohseni | |
| 11,006,876 B2 | 5/2021 | Johnson | |
| 11,006,878 B2 | 5/2021 | Johnson | |
| 11,137,283 B2 | 10/2021 | Balamurugan et al. | |
| 11,630,310 B2 | 4/2023 | Seidman et al. | |
| 2002/0033454 A1* | 3/2002 | Cheng | A61B 5/14546 250/339.12 |
| 2002/0195545 A1 | 12/2002 | Nishimura | |
| 2004/0057478 A1 | 3/2004 | Saito | |
| 2004/0064052 A1 | 4/2004 | Chance et al. | |
| 2004/0078216 A1 | 4/2004 | Toto | |
| 2004/0160996 A1 | 8/2004 | Giorgi et al. | |
| 2005/0038344 A1 | 2/2005 | Chance | |
| 2005/0061986 A1 | 3/2005 | Kardynal et al. | |
| 2005/0124863 A1 | 6/2005 | Cook | |
| 2005/0228291 A1 | 10/2005 | Chance | |
| 2006/0171845 A1 | 8/2006 | Martin | |
| 2006/0197452 A1 | 9/2006 | Zhang | |
| 2006/0264722 A1 | 11/2006 | Hannula et al. | |
| 2007/0038116 A1 | 2/2007 | Yamanaka | |
| 2007/0083097 A1 | 4/2007 | Fujiwara | |
| 2008/0021341 A1 | 1/2008 | Harris et al. | |
| 2009/0012402 A1 | 1/2009 | Mintz | |
| 2009/0054789 A1 | 2/2009 | Kiguchi et al. | |
| 2009/0163775 A1 | 6/2009 | Barrett | |
| 2009/0313048 A1 | 12/2009 | Kahn et al. | |
| 2010/0188649 A1* | 7/2010 | Prahl | G01S 7/4818 356/4.07 |
| 2010/0210952 A1 | 8/2010 | Taira et al. | |
| 2010/0249557 A1 | 9/2010 | Besko et al. | |
| 2010/0301194 A1 | 12/2010 | Patel | |
| 2011/0208675 A1 | 8/2011 | Shoureshi et al. | |
| 2011/0248175 A1 | 10/2011 | Frach | |
| 2012/0016635 A1 | 1/2012 | Brodsky et al. | |
| 2012/0029304 A1 | 2/2012 | Medina et al. | |
| 2012/0083673 A1 | 4/2012 | Al-Ali et al. | |
| 2012/0101838 A1 | 4/2012 | Lingard et al. | |
| 2013/0015331 A1 | 1/2013 | Birk | |
| 2013/0030267 A1 | 1/2013 | Lisogurski | |
| 2013/0030270 A1 | 1/2013 | Chiou et al. | |
| 2013/0032713 A1 | 2/2013 | Barbi et al. | |
| 2013/0090541 A1 | 4/2013 | MacFarlane et al. | |
| 2013/0144644 A1 | 6/2013 | Simpson | |
| 2013/0153754 A1 | 6/2013 | Drader et al. | |
| 2013/0221221 A1 | 8/2013 | Bouzid et al. | |
| 2013/0225953 A1 | 8/2013 | Oliviero et al. | |
| 2013/0342835 A1 | 12/2013 | Blacksberg | |
| 2014/0027607 A1 | 1/2014 | Mordarski et al. | |
| 2014/0028211 A1 | 1/2014 | Imam | |
| 2014/0055181 A1 | 2/2014 | Chavpas | |
| 2014/0066783 A1 | 3/2014 | Kiani | |
| 2014/0171757 A1 | 6/2014 | Kawato et al. | |
| 2014/0185643 A1 | 7/2014 | McComb et al. | |
| 2014/0191115 A1 | 7/2014 | Webster et al. | |
| 2014/0211194 A1 | 7/2014 | Pacala et al. | |
| 2014/0217264 A1 | 8/2014 | Shepard | |
| 2014/0275891 A1 | 9/2014 | Muehlemann et al. | |
| 2014/0289001 A1 | 9/2014 | Shelton | |
| 2014/0291481 A1 | 10/2014 | Zhang et al. | |
| 2015/0011848 A1* | 1/2015 | Ruchti | A61M 5/1723 600/316 |
| 2015/0038811 A1 | 2/2015 | Asaka | |
| 2015/0038812 A1 | 2/2015 | Ayaz et al. | |
| 2015/0041625 A1 | 2/2015 | Dutton | |
| 2015/0041627 A1 | 2/2015 | Webster | |
| 2015/0054111 A1 | 2/2015 | Niclass et al. | |
| 2015/0057511 A1 | 2/2015 | Basu | |
| 2015/0077279 A1 | 3/2015 | Song | |
| 2015/0094552 A1 | 4/2015 | Golda | |
| 2015/0150505 A1 | 6/2015 | Kaskoun et al. | |
| 2015/0157262 A1 | 6/2015 | Schuessler | |
| 2015/0157435 A1 | 6/2015 | Chasins et al. | |
| 2015/0182136 A1 | 7/2015 | Durduran et al. | |
| 2015/0192677 A1 | 7/2015 | Yu et al. | |
| 2015/0200222 A1 | 7/2015 | Webster | |
| 2015/0201841 A1 | 7/2015 | Ishikawa et al. | |
| 2015/0293224 A1 | 10/2015 | Eldada et al. | |
| 2015/0327777 A1 | 11/2015 | Kostic et al. | |
| 2015/0333095 A1 | 11/2015 | Fallica et al. | |
| 2015/0355019 A1 | 12/2015 | Nouri et al. | |
| 2015/0364635 A1 | 12/2015 | Bodlovic et al. | |
| 2016/0049765 A1 | 2/2016 | Eldada | |
| 2016/0099371 A1 | 4/2016 | Webster | |
| 2016/0119983 A1 | 4/2016 | Moore | |
| 2016/0150963 A1 | 6/2016 | Roukes et al. | |
| 2016/0161600 A1 | 6/2016 | Eldada et al. | |
| 2016/0181302 A1 | 6/2016 | McGarvey et al. | |
| 2016/0182902 A1 | 6/2016 | Guo | |
| 2016/0218236 A1 | 7/2016 | Dhulla et al. | |
| 2016/0247301 A1 | 8/2016 | Fang | |
| 2016/0278715 A1 | 9/2016 | Yu et al. | |
| 2016/0287107 A1 | 10/2016 | Szabados | |
| 2016/0296168 A1 | 10/2016 | Abreu | |
| 2016/0341656 A1 | 11/2016 | Liu et al. | |
| 2016/0345880 A1 | 12/2016 | Nakaji et al. | |
| 2016/0356718 A1 | 12/2016 | Yoon et al. | |
| 2016/0357260 A1 | 12/2016 | Raynor et al. | |
| 2017/0030769 A1 | 2/2017 | Clemens et al. | |
| 2017/0047372 A1 | 2/2017 | McGarvey et al. | |
| 2017/0052065 A1 | 2/2017 | Sharma et al. | |
| 2017/0085547 A1 | 3/2017 | De Aguiar et al. | |
| 2017/0118423 A1 | 4/2017 | Zhou et al. | |
| 2017/0124713 A1 | 5/2017 | Jurgenson et al. | |
| 2017/0131143 A1 | 5/2017 | Andreou et al. | |
| 2017/0139041 A1 | 5/2017 | Drader et al. | |
| 2017/0141100 A1 | 5/2017 | Tseng et al. | |
| 2017/0164857 A1 | 6/2017 | Soulet De Brugere | |
| 2017/0172447 A1 | 6/2017 | Mitra et al. | |
| 2017/0176579 A1 | 6/2017 | Niclass et al. | |
| 2017/0176596 A1 | 6/2017 | Shpunt et al. | |
| 2017/0179173 A1 | 6/2017 | Mandai et al. | |
| 2017/0186798 A1 | 6/2017 | Yang et al. | |
| 2017/0202518 A1 | 7/2017 | Furman et al. | |
| 2017/0265822 A1 | 9/2017 | Du | |
| 2017/0276545 A1 | 9/2017 | Henriksson | |
| 2017/0281086 A1* | 10/2017 | Donaldson | A61B 5/24 |
| 2017/0299700 A1 | 10/2017 | Pacala et al. | |
| 2017/0303789 A1 | 10/2017 | Tichauer et al. | |
| 2017/0314989 A1 | 11/2017 | Mazzillo et al. | |
| 2017/0338969 A1 | 11/2017 | Paul et al. | |
| 2017/0363467 A1 | 12/2017 | Clemens et al. | |
| 2017/0367650 A1 | 12/2017 | Wallois | |
| 2018/0003821 A1 | 1/2018 | Imai | |
| 2018/0014741 A1 | 1/2018 | Chou | |
| 2018/0019268 A1 | 1/2018 | Zhang et al. | |
| 2018/0020960 A1 | 1/2018 | Sarussi | |
| 2018/0026147 A1 | 1/2018 | Zhang et al. | |
| 2018/0027196 A1 | 1/2018 | Yang et al. | |
| 2018/0033895 A1 | 2/2018 | Mazzillo et al. | |
| 2018/0039053 A1 | 2/2018 | Kremer et al. | |
| 2018/0045816 A1 | 2/2018 | Jarosinski et al. | |
| 2018/0062345 A1 | 3/2018 | Bills et al. | |
| 2018/0066986 A1 | 3/2018 | Kasai et al. | |
| 2018/0069043 A1 | 3/2018 | Pan et al. | |
| 2018/0070830 A1 | 3/2018 | Sutin et al. | |
| 2018/0070831 A1 | 3/2018 | Sutin et al. | |
| 2018/0081061 A1 | 3/2018 | Mandai et al. | |
| 2018/0089531 A1 | 3/2018 | Geva et al. | |
| 2018/0089848 A1 | 3/2018 | Yang et al. | |
| 2018/0090526 A1 | 3/2018 | Mandal et al. | |
| 2018/0090536 A1 | 3/2018 | Mandai et al. | |
| 2018/0102442 A1 | 4/2018 | Wang et al. | |
| 2018/0103528 A1 | 4/2018 | Moore | |
| 2018/0103861 A1 | 4/2018 | Sutin et al. | |
| 2018/0117331 A1 | 5/2018 | Kuzniecky | |
| 2018/0120152 A1 | 5/2018 | Leonardo | |
| 2018/0122560 A1 | 5/2018 | Okuda | |
| 2018/0156660 A1 | 6/2018 | Turgeon | |
| 2018/0167606 A1 | 6/2018 | Cazaux et al. | |

(56) References Cited

U.S. PATENT DOCUMENTS

| | | |
|---|---|---|
| 2018/0175230 A1 | 6/2018 | Droz et al. |
| 2018/0180473 A1 | 6/2018 | Clemens et al. |
| 2018/0185667 A1 | 7/2018 | Huang |
| 2018/0217261 A1 | 8/2018 | Wang |
| 2018/0296094 A1 | 10/2018 | Nakamura |
| 2018/0366342 A1 | 12/2018 | Inoue et al. |
| 2019/0006399 A1 | 1/2019 | Otake et al. |
| 2019/0025406 A1 | 1/2019 | Krelboim et al. |
| 2019/0026849 A1 | 1/2019 | Demeyer |
| 2019/0088697 A1 | 3/2019 | Furukawa et al. |
| 2019/0091483 A1 | 3/2019 | Deckert |
| 2019/0113385 A1 | 4/2019 | Fukuchi |
| 2019/0120975 A1 | 4/2019 | Ouvrier-Buffet |
| 2019/0167211 A1 | 6/2019 | Everman et al. |
| 2019/0175068 A1 | 6/2019 | Everdell |
| 2019/0192031 A1 | 6/2019 | Laszlo et al. |
| 2019/0200888 A1 | 7/2019 | Poltorak |
| 2019/0209012 A1 | 7/2019 | Yoshimoto et al. |
| 2019/0239753 A1 | 8/2019 | Wentz |
| 2019/0261869 A1 | 8/2019 | Franceschini |
| 2019/0298158 A1 | 10/2019 | Dhaliwal |
| 2019/0343395 A1 | 11/2019 | Cussac |
| 2019/0355773 A1 | 11/2019 | Field et al. |
| 2019/0355861 A1 | 11/2019 | Katnani |
| 2019/0363210 A1 | 11/2019 | Do Valle |
| 2019/0378869 A1 | 12/2019 | Field et al. |
| 2019/0388018 A1 | 12/2019 | Horstmeyer |
| 2019/0391213 A1 | 12/2019 | Alford |
| 2020/0022581 A1* | 1/2020 | Vanegas ............. A61B 5/1118 |
| 2020/0041727 A1 | 2/2020 | Yamamoto |
| 2020/0044098 A1 | 2/2020 | Azuma |
| 2020/0056263 A1 | 2/2020 | Bhattacharyya |
| 2020/0057115 A1 | 2/2020 | Jiménez-Martínez |
| 2020/0057116 A1 | 2/2020 | Zorzos et al. |
| 2020/0057146 A1 | 2/2020 | Steinkogler et al. |
| 2020/0060542 A1 | 2/2020 | Alford |
| 2020/0088811 A1 | 3/2020 | Mohseni |
| 2020/0109481 A1 | 4/2020 | Sobek |
| 2020/0123416 A1 | 4/2020 | Bhattacharyya |
| 2020/0136632 A1 | 4/2020 | Lin |
| 2020/0182692 A1 | 6/2020 | Lilic |
| 2020/0188030 A1 | 6/2020 | Kopper et al. |
| 2020/0191883 A1 | 6/2020 | Bhattacharyya |
| 2020/0196932 A1 | 6/2020 | Johnson et al. |
| 2020/0241094 A1 | 7/2020 | Alford |
| 2020/0253479 A1 | 8/2020 | Nurmikko |
| 2020/0256929 A1 | 8/2020 | Ledbetter et al. |
| 2020/0309873 A1 | 10/2020 | Ledbetter et al. |
| 2020/0315510 A1 | 10/2020 | Johnson |
| 2020/0334559 A1 | 10/2020 | Anderson |
| 2020/0337624 A1 | 10/2020 | Johnson |
| 2020/0341081 A1 | 10/2020 | Mohseni et al. |
| 2020/0348368 A1 | 11/2020 | Garber et al. |
| 2020/0381128 A1 | 12/2020 | Pratt |
| 2020/0390358 A1 | 12/2020 | Johnson |
| 2020/0393902 A1 | 12/2020 | Mann et al. |
| 2020/0400763 A1 | 12/2020 | Pratt |
| 2021/0015385 A1 | 1/2021 | Katnani |
| 2021/0011094 A1 | 2/2021 | Bednarke |
| 2021/0041512 A1 | 2/2021 | Pratt |
| 2021/0063510 A1 | 3/2021 | Ledbetter |
| 2021/0013974 A1 | 5/2021 | Seidman |
| 2021/0139742 A1 | 5/2021 | Seidman |
| 2021/0223098 A1 | 7/2021 | Ledvina et al. |
| 2021/0265512 A1 | 8/2021 | Ayel |
| 2021/0290064 A1 | 9/2021 | Do Valle |
| 2021/0294996 A1 | 9/2021 | Field |

FOREIGN PATENT DOCUMENTS

| | | | |
|---|---|---|---|
| EP | 0656536 | 4/2004 | |
| EP | 2294973 | 3/2011 | |
| EP | 3419168 | 12/2018 | |
| EP | 3487072 | 5/2019 | |
| FR | 3011932 A1 * | 4/2015 | ......... G01N 21/6408 |
| JP | 2012125370 A * | 7/2012 | |
| KR | 20170087639 A | 7/2017 | |
| WO | 8804034 | 6/1988 | |
| WO | 1999053577 | 10/1999 | |
| WO | 2008144831 | 12/2008 | |
| WO | 2011083563 | 7/2011 | |
| WO | 2012135068 | 10/2012 | |
| WO | 2013034770 | 3/2013 | |
| WO | 2013066959 | 5/2013 | |
| WO | 2015052523 | 4/2015 | |
| WO | 2015109005 | 7/2015 | |
| WO | 2016166002 | 10/2016 | |
| WO | 2017004663 | 1/2017 | |
| WO | 2017083826 | 5/2017 | |
| WO | 2017130682 | 8/2017 | |
| WO | 2017150146 | 9/2017 | |
| WO | 2017203936 | 11/2017 | |
| WO | 2018007829 | 1/2018 | |
| WO | 2018033751 | 2/2018 | |
| WO | 2018122560 | 7/2018 | |
| WO | 2019221784 | 11/2019 | |

OTHER PUBLICATIONS

Bellis, Stephen et al.,"Photon counting imaging: the DigitalAPD," Society of Photo-Optical Instrumentation Engineers (SPIE) Conference Series, Feb. 2006, vol. 6068, pp. 111-120.

Blutman, et al.,"A 0.1 pJ Freeze Vernier Time-to-Digital Converter in 65nm CMOS," 2014 International Symposium on Circuits and Systems (ISCAS), Melbourne, Australia.

Cambie, Dario et al.,"Every photon counts: understanding and optimizing photon paths in luminescent solar concentrator-based photomicroreactors (LSC-PMs)," React. Chem. Eng., 2017, 2, 561-566.

Contini, et al.,"Photon migration through a turbid slab described by a model based on diffusion approximation. I. Theory," Appl. Opt. 36(19), 4587 (1997).

Dalla Mora, et al.,"Fast-Gated Single-Photon Avalanche Diode for Wide Dynamic Range Near Infrared Spectroscopy," IEEE Journal of Selected Topics in Quantum Electronics, vol. 16, No. 4, Jul./Aug. 2010 ,2010 , 1023-1030.

Dalla Mora, et al.,"Memory effect in silicon time-gated single-photon avalanche diodes," http://dx.doi.org/10.1063/1.4915332, Journal of Applied Physics 117, 114501, 2015 ,2015 ,1-7.

De Heyn, et al.,"A fast start-up 3GHz-10GHz digitally controlled oscillator for UWB impulse radio in 90nm CMOS," 2007 European Solid-State Circuits Conference—(ESSCIRC), Munich, Germany, pp. 484-487.

Di Sieno, et al.,"Probe-hosted large area silicon photomultiplier and high-throughput timing electronics for enhanced performance time-domain functional near-infrared spectroscopy," Biomed. Opt. Express 11(11), 6389 (2020).

Dutton, et al.,"A Time-Correlated Single-Photon-Counting Sensor with 14GS/s Histogramming Time-to-Digital Converter," 2015 IEEE International Solid-State Circuits Conference ISSCC 2015 / Session 11 / Sensors and Imagers for Life Sciences / 11.5.

Fishburn, et al.,"Temporal Derivative Distribution Repair (TDDR): A motion correction method for fNIRS," Neuroimage. Jan. 1, 2019; 184: 171-179. doi:10.1016/j.neuroimage.2018.09.025.

Fisher, et al.,"A Reconfigurable Single-Photon-Counting Integrating Receiver for Optical Communications," IEEE Journal of Solid-State Circuits, vol. 48, No. 7, Jul. 2013, https://www.researchgate.net/publication/260626902.

Gallivanoni, et al.,"Progress in Quenching Circuits for Single Photon Avalanche Diodes," IEEE Transactions on Nuclear Science, vol. 57, No. 6, Dec. 2010.

Gnecchi, et al.,"A 1×16 SIPM Array for Automotive 3D Imaging LiDAR Systems."

Harmon, Eric S. et al.,"Compound Semiconductor SPAD Arrays, LightSpin Technologies," http://www.lightspintech.com/publications.html.

Henderson, et al.,"A 192 x 128 Time Correlated SPAD Image Sensor in 40-nm CMOS Technology," IEEE Journal of Solid-State Circuits, IEEE Journal of Solid-State Circuits, 2019.

(56) References Cited

OTHER PUBLICATIONS

Henderson, et al.,"A 256×256 40nm/90nm CMOS 3D-Stacked 120dB Dynamic-Range Reconfigurable Time-Resolved SPAD Imager," 2019 IEEE International Solid-State Circuits Conference—(ISSCC), San Francisco, CA, USA, 2019, pp. 106-108. doi: 10.1109/ISSCC.2019.8662355.

Huppert, et al.,"HomER: a review of time-series analysis methods for near-infrared spectroscopy of the brain," Appl. Opt. 48(10), D280 (2009).

Kienle, et al.,"Improved solutions of the steady-state and the time-resolved diffusion equations for reflectance from a semi-infinite turbid medium," J. Opt. Soc. Am. A 14(1), 246 (1997).

Konugolu, et al.,"Broadband (600-1350 nm) Time-Resolved Diffuse Optical Spectrometer for Clinical Use," IEEE Journal of Selected Topics in Quantum Electronics, vol. 22, No. 3, May/Jun. 2016.

Lacerenza, et al.,"Wearable and wireless time-domain near-infrared spectroscopy system for brain and muscle hemodynamic monitoring," Biomed. Opt. Express 11(10), 5934 (2020).

Lange, et al.,"Clinical Brain Monitoring with Time Domain NIRS: A Review and Future Perspectives," Applied Sciences 9(8), 1612 (2019).

Lange, et al.,"MAESTROS: A Multiwavelength Time-Domain NIRS System to Monitor Changes in Oxygenation and Oxidation State of Cytochrome-C-Oxidase," IEEE J. Select. Topics Quantum Electron. 25(1), 1-12 (2019).

Lee, et al.,"High-Performance Back-Illuminated Three-Dimensional Stacked Single-Photon Avalanche Diode Implemented in 45-nm CMOS Technology," IEEE Journal of Selected Topics in Quantum Electronics 6, 1-9 (2018).

Mandai, et al.,"A 4 X 4 X 416 digital SIPM array with 192 TDCs for multiple high-resolution timestamp acquisition," 2013 JINST 8 PO5024.

Martelli, et al.,"Optimal estimation reconstruction of the optical properties of a two-layered tissue phantom from time-resolved single-distance measurements," Journal of Biomedical Optics 20(11), 115001 (Nov. 2015).

Maruyama, et al.,"A 1024 x 8, 700-ps Time-Gated SPAD Line Sensor for Planetary Surface Exploration With Laser Raman Spectroscopy and LIBS," IEEE Journal of Solid-State Circuits, vol. 49, No. 1, Jan. 2014 ,2014 , 179-189.

Mita, et al.,"High-Speed and Compact Quenching Circuit for Single-Photon Avalanche Diodes," IEEE Transactions on Instrumentation and Measurement, vol. 57, No. 3, Mar. 2008. pp. 543-547.

Mora, et al.,"Fast silicon photomultiplier improves signal harvesting and reduces complexity in time-domain diffuse optics," Opt. Express 23(11), 13937 (2015).

Mora, Alberto D. et al.,"Fast-Gated Single-Photon Avalanche Diode for Wide Dynamic Range Near Infrared Spectroscopy," IEEE Journal of Selected Topics in Quantum Electronics, vol. 16, No. 4, pp. 1023-1030, Jul./Aug. 2010.

Parmesan, et al.,"A 256 x 256 SPAD array with in-pixel Time to Amplitude Conversion for Fluorescence Lifetime Imaging Microscopy," 2015.

Pifferi, et al.,"Performance assessment of photon migration instruments: the MEDPHOT protocol," Applied Optics, 44(11), 2104-2114.

Prahl, et al.,"Optical Absorption of Hemoglobin," http://omic.ogi.edu/spectra/hemoglobin/index.html.

Puszka, et al.,"Time-resolved diffuse optical tomography using fast-gated single-photon avalanche diodes," Biomedical optics express, 2013, vol. 4, No. 8, pp. 1351-1365 (Year: 2013).

Re, et al.,"Multi-channel medical device for time domain functional near infrared spectroscopy based on wavelength space multiplexing," Biomed. Opt. Express 4(10), 2231 (2013).

Renna, et al.,"Eight-Wavelength, Dual Detection Channel Instrument for Near-Infrared Time-Resolved Diffuse Optical Spectroscopy," IEEE J. Select. Topics Quantum Electron. 25(1), 1-11 (2019).

Richardson, et al.,"A 32x32 50ps resolution 10 bit time to digital converter array in 130nm CMOS for time correlated imaging," CICC 2009 Proceedings of the IEEE 2009 Custom Integrated Circuits Conference. IEEE Society, San Jose, U.S.A., pp. 77-80, CICC 2009, San Jose, U.S.A., Sep. 13, 2009. https://doi.org/doi:10.1109/CICC.2009.5280890.

Takai, et al.,"Single-Photon Avalanche Diode with Enhanced NIR-Sensitivity for Automotive LIDAR Systems," Sensors, 2016, 16(4): 459, pp. 1-9 (Year: 2016).

Torricelli, et al.,"Time domain functional NIRS imaging for human brain mapping," NeuroImage 85, 28-50 (2014).

Wabnitz, et al.,"Depth-selective data analysis for time-domain fNIRS: moments vs. time windows," Biomed. Opt. Express 11(8), 4224 (2020).

Wabnitz, et al.,"Performance assessment of time-domain optical brain imagers, part 1: basic instrumental performance protocol," Journal of Biomedical Optics 19(8), 086010 (Aug. 2014).

Wabnitz, et al.,"Performance assessment of time-domain optical brain imagers, part 2: nEUROPt protocol," Journal of Biomedical Optics 19(8), 086012 (Aug. 2014).

Wojtkiewicz, et al.,"Self-calibrating time-resolved near infrared spectroscopy," Biomed. Opt. Express 10(5), 2657 (2019).

Zhang, et al.,"A CMOS SPAD Imager with Collision Detection and 128 Dynamically Reallocating TDCs for Single-Photon Counting and 3D Time-of-Flight Imaging," Sensors (Basel, Switzerland), 18(11), 4016. doi:10.3390/s18114016.

Zucchelli, et al.,"Method for the discrimination of superficial and deep absorption variations by time domain fNIRS," 2013 OSA Dec. 1, 2013 | vol. 4, No. 12 | DOI:10.1364/BOE.4.002893 | Biomedical Optics Express 2893.

Alayed, et al.,"Characterization of a Time-Resolved Diffuse Optical Spectroscopy Prototype Using Low-Cost, Compact Single Photon Avalanche Detectors for Tissue Optics Applications," Sensors 2018, 18, 3680; doi:10.3390/s18113680, Oct. 29, 2018.

Bellis, et al.,"Photon counting imaging: the DigitalAPD," Society of Photo-Optical Instrumentation Engineers (SPIE) Conference Series, Feb. 2006, vol. 6068, pp. 111-120.

Blutman, et al.,"A 0.1 pJ Freeze Vernier Time-to-Digital Converter in 65nm CMOS," 2014 International Symposium on Circuits and Systems (ISCAS), Melbourne, Australia, Jun. 1-5, 2014.

Cambie, et al.,"Every photon counts: understanding and optimizing photon paths in luminescent solar concentrator-based photomicroreactors (LSC-PMs)," React. Chem. Eng., 2017, 2, 561-566.

Dalla Mora, et al.,"Fast-Gated Single-Photon Avalanche Diode for Wide Dynamic Range Near Infrared Spectroscopy," IEEE Journal of Selected Topics in Quantum Electronics, vol. 16, No. 4, Jul./Aug. 2010.

Dalla Mora, et al.,"Memory effect in silicon time-gated single-photon avalanche diodes," http://dx.doi.org/10.1063/1.4915332, Journal of Applied Physics 117, 114501, 2015.

De Heyn, et al.,"A fast start-up 3GHz-10GHz digitally controlled oscillator for UWB impulse radio in 90nm CMOS," 2007 European Solid-State Circuits Conference—(ESSCIRC), Munich, Germany, pp. 484-487, Sep. 11-13, 2007.

Dutton, et al.,"A Time-Correlated Single-Photon-Counting Sensor with 14GS/s Histogramming Time-to-Digital Converter," 2015 IEEE International Solid-State Circuits Conference ISSCC 2015 / Session 11 / Sensors and Imagers for Life Sciences / 11.5, Feb. 22-26, 2015.

Gnecchi, et al.,"A 1×16 SIPM Array for Automotive 3D Imaging LiDAR Systems.", *Proceedings of the 2017 International Image Sensor Workshop (IISW)*, Hiroshima, Japan (2017).

Harmon, et al.,"Compound Semiconductor SPAD Arrays," LightSpin Technologies, http://www.lightspintech.com/publications.html (2013).

Henderson, et al.,"A 192 x 128 Time Correlated SPAD Image Sensor in 40-nm CMOS Technology," IEEE Journal of Solid-State Circuits, 2019.

Lange, et al.,"MAESTROS: A Multiwavelength Time-Domain NIRS System to Monitor Changes in Oxygenation and Oxidation State of Cytochrome-C-Oxidase," IEEE J. Select. Topics Quantum Electron. 25(1), 1-12 (2019).

Mandai, et al.,"A 4 X 4 X 416 digital SIPM array with 192 TDCs for multiple high-resolution timestamp acquisition," 2013 JINST 8 PO5024, May 31, 2013.

(56) References Cited

OTHER PUBLICATIONS

Maruyama, et al.,"A 1024 x 8, 700-ps Time-Gated SPAD Line Sensor for Planetary Surface Exploration With Laser Raman Spectroscopy and LIBS," IEEE Journal of Solid-State Circuits, vol. 49, No. 1, Jan. 2014.
Mora, et al.,"Fast-Gated Single-Photon Avalanche Diode for Wide Dynamic Range Near Infrared Spectroscopy," IEEE Journal of Selected Topics in Quantum Electronics, vol. 16, No. 4, pp. 1023-1030, Jul./Aug. 2010.
Parmesan, et al.,"A 256 x 256 SPAD array with in-pixel Time to Amplitude Conversion for Fluorescence Lifetime Imaging Microscopy,", *Memory 900.M4*, 2015.
Pifferi, et al.,"Performance assessment of photon migration instruments: the MEDPHOT protocol," Applied Optics, 44(11), 2104-2114 (2005).
Prahl, et al.,"Optical Absorption of Hemoglobin," http:/omic.ogi.edu/spectra/hemoglobin/index.html (1999).
Zhang, et al.,"A CMOS SPAD Imager with Collision Detection and 128 Dynamically Reallocating TDCs for Single-Photon Counting and 3D Time-of-Flight Imaging," Sensors (Basel, Switzerland), 18(11), 4016. doi:10.3390/s18114016 Nov. 17, 2018.
International Search Report and Written Opinion received in International Application No. PCT/2020/027537, dated Sep. 7, 2020.
International Search Report and Written Opinion received in International Application No. PCT/2020/028820, dated Aug. 26, 2020.
International Search Report and Written Opinion received in International Application No. PCT/US20/34062, dated Aug. 26, 2020.
International Search Report and Written Opinion received in International Application No. PCT/US2018/058580, dated Feb. 12, 2019.
International Search Report and Written Opinion received in International Application No. PCT/US2018/062777, dated Feb. 13, 2019.
International Search Report and Written Opinion received in International Application No. PCT/US2019/019317, dated May 28, 2019.
Non-Final Office Action received in U.S. Appl. No. 16/177,351, dated Apr. 1, 2019.
Non-Final Office Action received in U.S. Appl. No. 16/283,730, dated May 16, 2019.
Non-Final Office Action received in U.S. Appl. No. 16/370,991, dated Feb. 10, 2020.
Non-Final Office Action received in U.S. Appl. No. 16/537,360, dated Feb. 25, 2020.
Non-Final Office Action received in U.S. Appl. No. 16/544,850, dated Jun. 25, 2020.
Non-Final Office Action received in U.S. Appl. No. 16/856,524, dated Dec. 1, 2020.
Partial Search Report received in International Application No. PCT/2020/028820, dated Jul. 1, 2020.
Partial Search Report received in International Application No. PCT/US2020/027537, dated Jul. 17, 2020.
Chen, et al., "A PVT Insensitive Field Programmable Gate Array Time-to-digital Converter", 2013 IEEE Nordic-Mediterranean Workshop on Time-To-Digital Converters. Oct. 3, 2013.
Field, et al., "A 100-fps, Time-Correlated Single-PhotonCounting-Based Fluorescence-Lifetime Imager in 130-nm CMOS", IEEE Journal of Solid-State Circuits, vol. 49, No. 4, Apr. 2014.
Lebid, et al., "Multi-Timescale Measurements of Brain Responses in Visual Cortex During Functional Stimulation Using Time-Resolved Spectroscopy", SPIE vol. 5826. Dec. 31, 2005. p. 609, last paragraph—p. 610, paragraph 1.
Zheng, et al., "An Integrated Bias Voltage Control Method for SPAD Arrays", Oct. 1, 2018, IEEE Service Center.
"emojipedia.org", https://emojipedia.org (accessed May 27, 2021).
"International Search Report and Written Opinion received in International Application No. PCT/2021/018188".
"International Search Report and Written Opinion received in International Application No. PCT/US2021/018155".
"International Search Report and Written Opinion received in International Application No. PCT/US2021/018187".
"International Search Report and Written Opinion received in International Application No. PCT/US2021/018190".
"scienceofpeople.com/emojis", https://www.scienceofpeople.com/emojis/ (accessed May 27, 2021).
Hebert, et al.,"Spatiotemporal image correlation spectroscopy (STICS) theory, verification, and application to protein velocity mapping in living CHO cells", Biophysical journal 88, No. 5 (2005): 3601-3614.
Kheng, et al.,"Image Processing", https://www.comp.nus.edu.sg/~cs4243/lecture/imageproc.pdf, Mar. 9, 2014.
Sneha, et al.,"Understanding Correlation", https://www.allaboutcircuits.com/technical-articles/understanding-correlation/, Jan. 4, 2017.
Xu, et al.,"A 655 µW Silicon Photomultiplier-Based NIRS/EEG/EIT Monitoring ASIC for Wearable Functional Brain Imaging", IEEE Transactions on Biomedical Circuits and Systems, IEEE, US, vol. 12, No. 6, Dec. 1, 2018.
Zucconi, et al., "The Autocorrelation Function", https://www.alanzucconi.com/2016/06/06/autocorrelation-function/, Jun. 6, 2016.

\* cited by examiner

ESTIMATION OF SOURCE-DETECTOR SEPARATION IN AN OPTICAL MEASUREMENT SYSTEM

RELATED APPLICATIONS

The present application claims priority under 35 U.S.C. § 119(e) to U.S. Provisional Patent Application No. 63/071,473, filed on Aug. 28, 2020, and to U.S. Provisional Patent Application No. 62/992,543, filed on Mar. 20, 2020, and to U.S. Provisional Patent Application No. 62/979,866, filed on Feb. 21, 2020. These applications are incorporated herein by reference in their respective entireties.

BACKGROUND INFORMATION

Detecting neural activity in the brain (or any other turbid medium) is useful for medical diagnostics, imaging, neuroengineering, brain-computer interfacing, and a variety of other diagnostic and consumer-related applications. For example, it may be desirable to detect neural activity in the brain of a user to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. One technique to measure such responses is time-correlated single-photon counting (TCSPC). Time-correlated single-photon counting detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Optical measurement systems and methods are described herein. An exemplary optical measurement system includes a first light source, a second light source, a first detector, a second detector, and a processing unit. The first light source is configured to emit a first light pulse toward a target, and the second light source is configured to emit a second light pulse toward the target. The processing unit is configured to determine a plurality of temporal distributions of photons included in the first light pulse and the second light pulse and detected by the first detector and the second detector after the photons are scattered by the target. The processing unit is further configured to determine, based on the plurality of temporal distributions, a distance between the first light source and the second detector.

The systems and methods described herein provide various benefits. For example, the propagation of light through a turbid medium (e.g., the brain) may be modeled by a standard model of diffusion theory. In such a model, the scattering of light in the target depends on, among other things, the distance between the light source and the detector. When the distance between the source and the detector is known, the diffusion theory model can be used to infer spatial (e.g., depth localization) information about the detected signals (e.g., neural activity and/or other attributes of the brain). With the systems and methods described herein, the distance separating a light source and one or more detectors does not need to be known in advance. Rather, the separation distance can be determined analytically from the time-domain information detected by the detector. Moreover, the ability to analytically determine the source-detector distance eliminates any need for a fixed or static configuration of sources and detectors (or of wearable modules containing the sources and detectors). Instead, the optical measurement systems described herein may be embodied in a flexible, wearable device in which the light source-detector distance may vary, whether due the three-dimensional geometry of the user's body, targeting specific regions of the user, or any other reason. Thus, the optical measurement systems described herein may perform a calibration procedure, after the wearable device (e.g., headset) is placed on the user's head, to determine where the sources and detectors (or wearable modules) are located relative to one another during operation. These and other advantages and benefits of the present systems and methods are described more fully herein and/or will be made apparent in the description herein.

Figure 1:
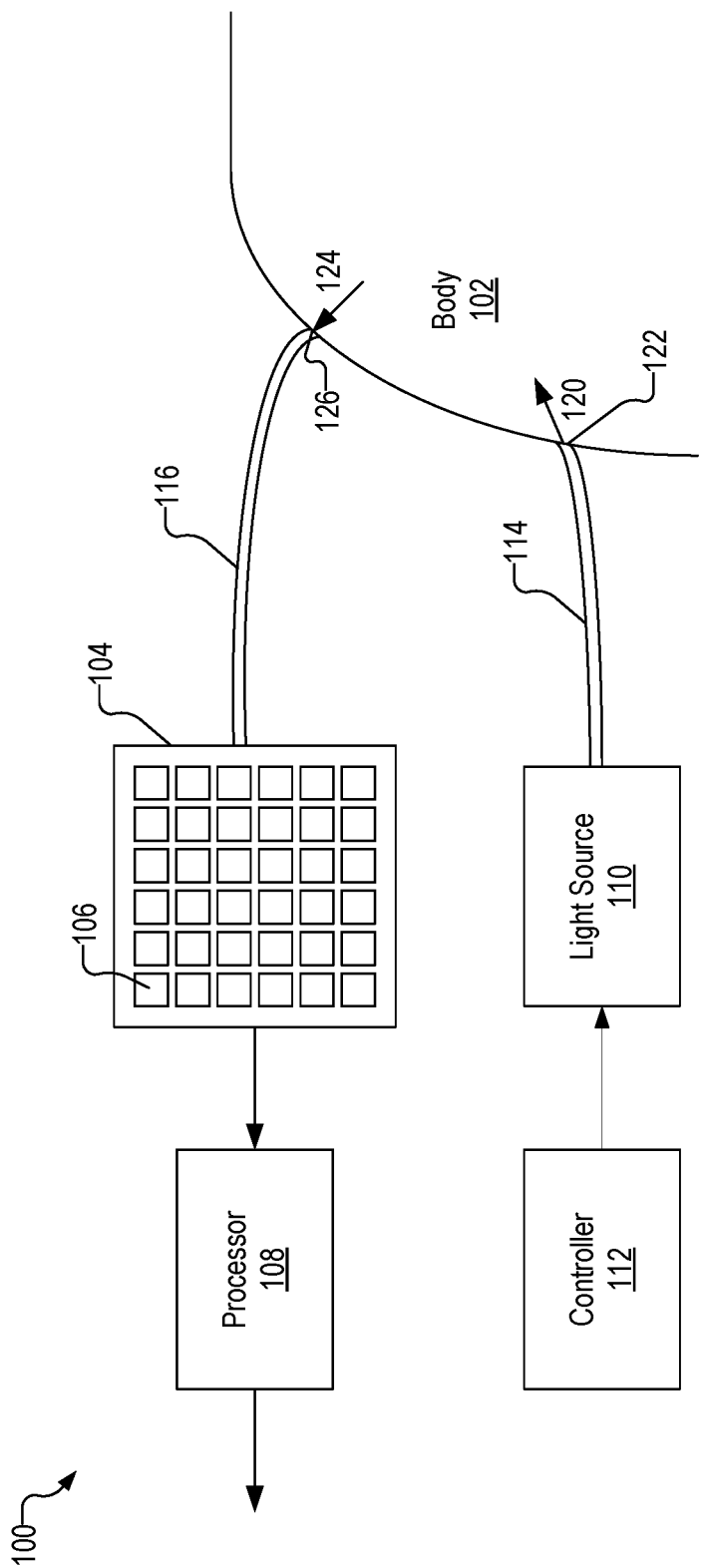
FIG. 1 illustrates an exemplary optical measurement system.

FIG. 1 shows an exemplary optical measurement system 100 configured to perform an optical measurement operation with respect to a body 102. Optical measurement system 100 may, in some examples, be portable and/or wearable by a user.

In some examples, optical measurement operations performed by optical measurement system 100 are associated with a time domain-based optical measurement technique. Example time domain-based optical measurement techniques include, but are not limited to, TCSPC, time domain near infrared spectroscopy (TD-NIRS), time domain diffusive correlation spectroscopy (TD-DCS), and time domain digital optical tomography (TD-DOT).

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light guides, as described more fully herein). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as 2ⁿ photodetectors (e.g., 256, 512, ..., 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes, distributed feedback (DFB) lasers, super luminescent diodes (SLDs), light emitting diodes (LEDs), diode-pumped solid-state (DPSS) lasers, super luminescent light emitting diode (sLEDs), vertical-cavity surface-emitting lasers (VCSELs), titanium sapphire lasers, a micro light emitting diodes (mLEDs), and/or any other suitable laser or light source configured to emit light in one or more discrete wavelengths or narrow wavelength bands. In some examples, the light emitted by light source 110 is high coherence light (e.g., light that has a coherence length of at least 5 centimeters) at a predetermined center wavelength. In some examples, the light emitted by light source 110 is emitted as a plurality of alternating light pulses of different wavelengths.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 travels via an optical conduit 114 (e.g., a light pipe, a light guide, a waveguide, a single-mode optical fiber, and/or or a multi-mode optical fiber) to body 102 of a subject. Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by arrow 120, light emitted by light source 110 enters body 102 at a first location 122 on body 102. Accordingly, a distal end of optical conduit 114 may be positioned at (e.g., right above, in physical contact with, or physically attached to) first location 122 (e.g., to a scalp of the subject). In some examples, the light may emerge from optical conduit 114 and spread out to a certain spot size on body 102 to fall under a predetermined safety limit. At least a portion of light indicated by arrow 120 may be scattered within body 102.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a light guide, a waveguide, a single-mode optical fiber, and/or a multi-mode optical fiber) is positioned at (e.g., right above, in physical contact with, or physically attached to) output location 126 on body 102. In this manner, optical conduit 116 may collect at least a portion of the scattered light (indicated as light 124) as it exits body 102 at location 126 and carry light 124 to detector 104. Light 124 may pass through one or more lenses and/or other optical elements (not shown) that direct light 124 onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., tissue, blood flow, etc.) in body 102. Example embodiments of accumulated outputs are described herein.

Figure 2:
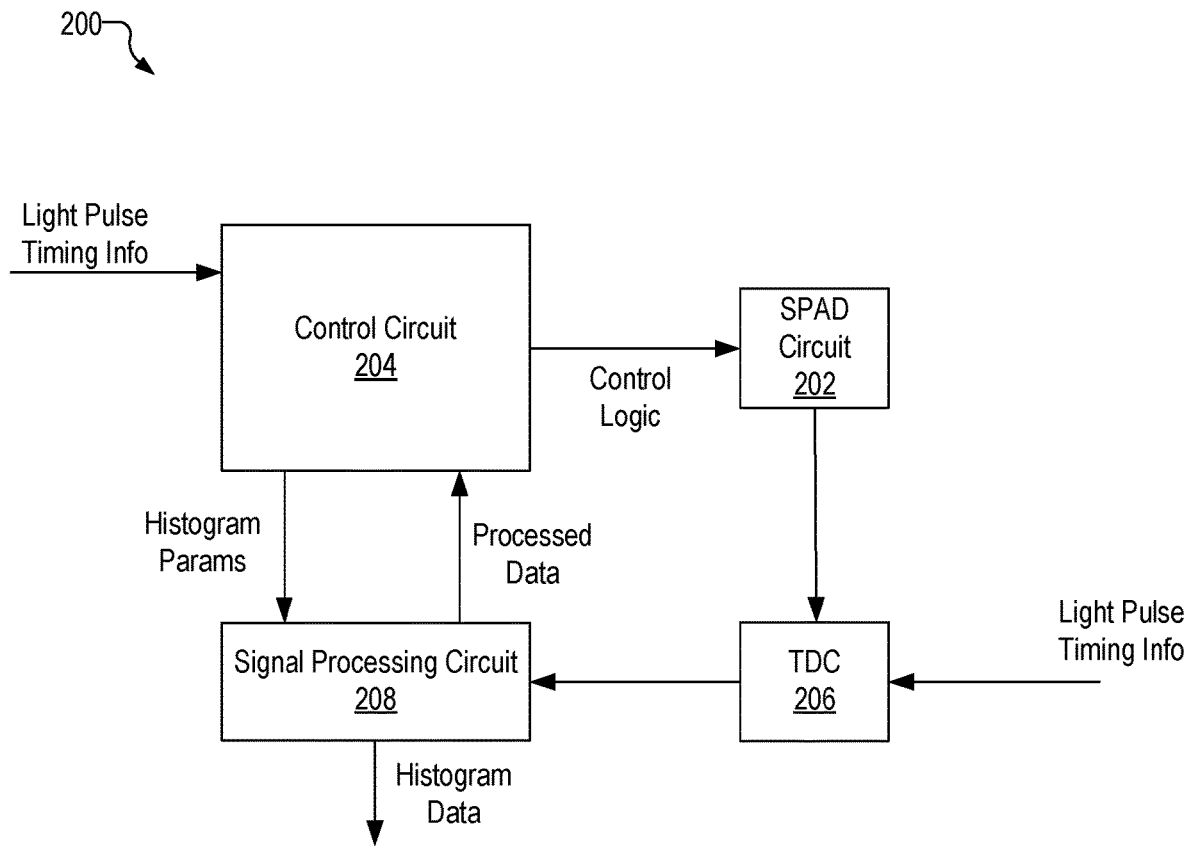
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 includes a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, which are incorporated herein by reference in their entireties.

In some alternative configurations, SPAD circuit 202 does not include a fast gating circuit. In these configurations, the SPAD included in SPAD circuit 202 may be gated in any suitable manner.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 102). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for one or more SPAD circuits 202 and/or TDCs 206.

Figure 3:
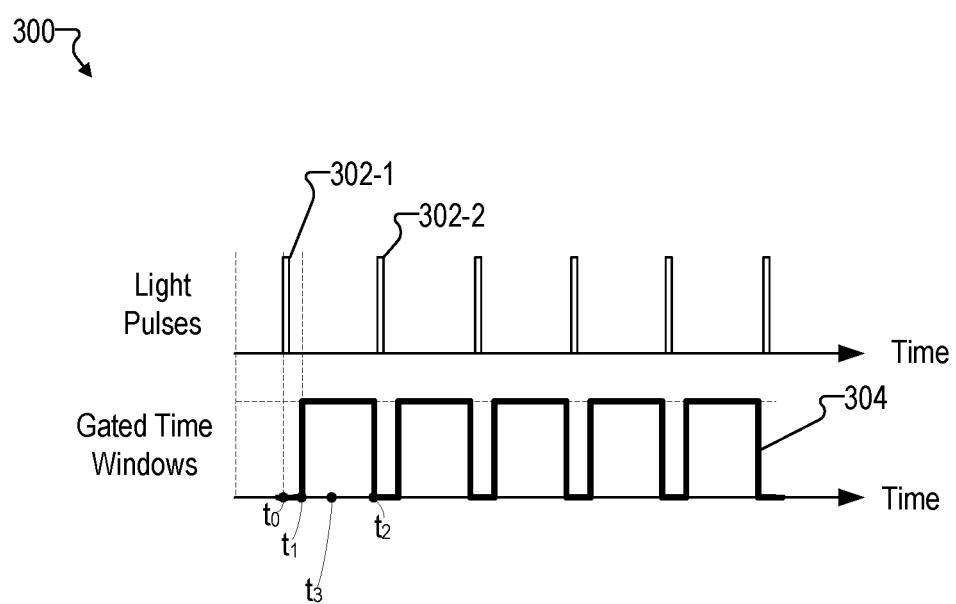
FIG. 3 illustrates an exemplary timing diagram for performing an optical measurement operation using an optical measurement system.

FIG. 3 illustrates an exemplary timing diagram 300 for performing an optical measurement operation using optical measurement system 100. The optical measurement operation may be performed in accordance with a time domain-based technique, such as TD-NIRS. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and at least a portion of the scattered light may be detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

Timing diagram 300 shows a sequence of light pulses 302 (e.g., light pulses 302-1 and 302-2) that may be applied to the target (e.g., tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons. As shown, light pulse 302-1 is applied at a time $t_0$. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time $t_0$, which may minimize photons detected directly from the laser pulse, before the laser pulse reaches the target. However, in some alternative examples, time $t_1$ is set to be equal to time $t_0$.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

Figure 4:
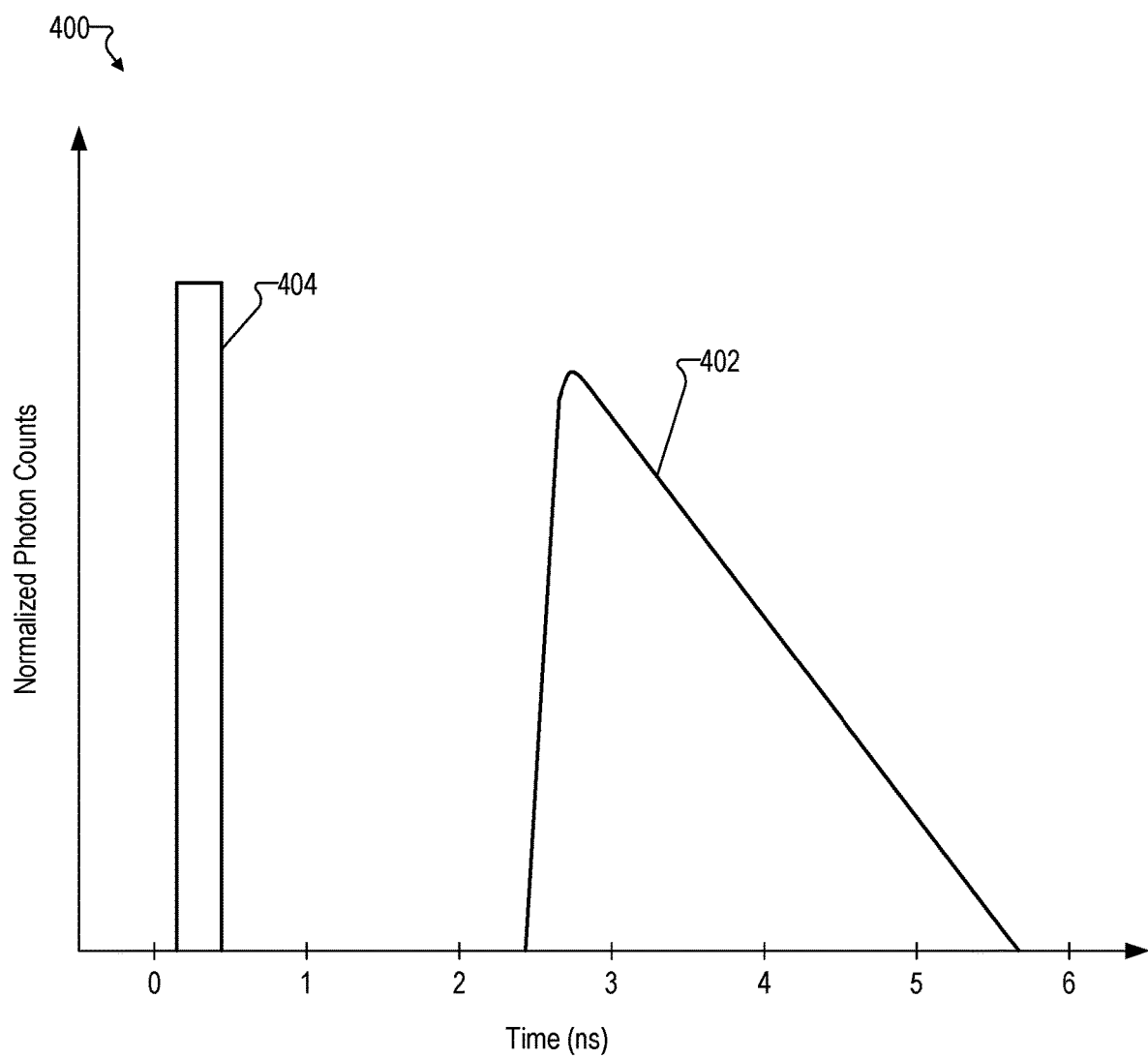
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer biological (e.g., neural) activity.

Optical measurement system 100 may be implemented by or included in any suitable device(s). For example, optical measurement system 100 may be included in a non-wearable device (e.g., a medical device and/or consumer device that is placed near the head or other body part of a user to perform one or more diagnostic, imaging, and/or consumer-related operations). Optical measurement system 100 may alternatively be included, in whole or in part, in a sub-assembly enclosure of a wearable invasive device (e.g., an implantable medical device for brain recording and imaging).

Alternatively, optical measurement system 100 may be included, in whole or in part, in a non-invasive wearable device that a user may wear to perform one or more diagnostic, imaging, analytical, and/or consumer-related operations. The non-invasive wearable device may be placed on a user's head or other part of the user to detect neural activity. In some examples, such neural activity may be used to make behavioral and mental state analysis, awareness and predictions for the user.

Mental state described herein refers to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Figure 5:
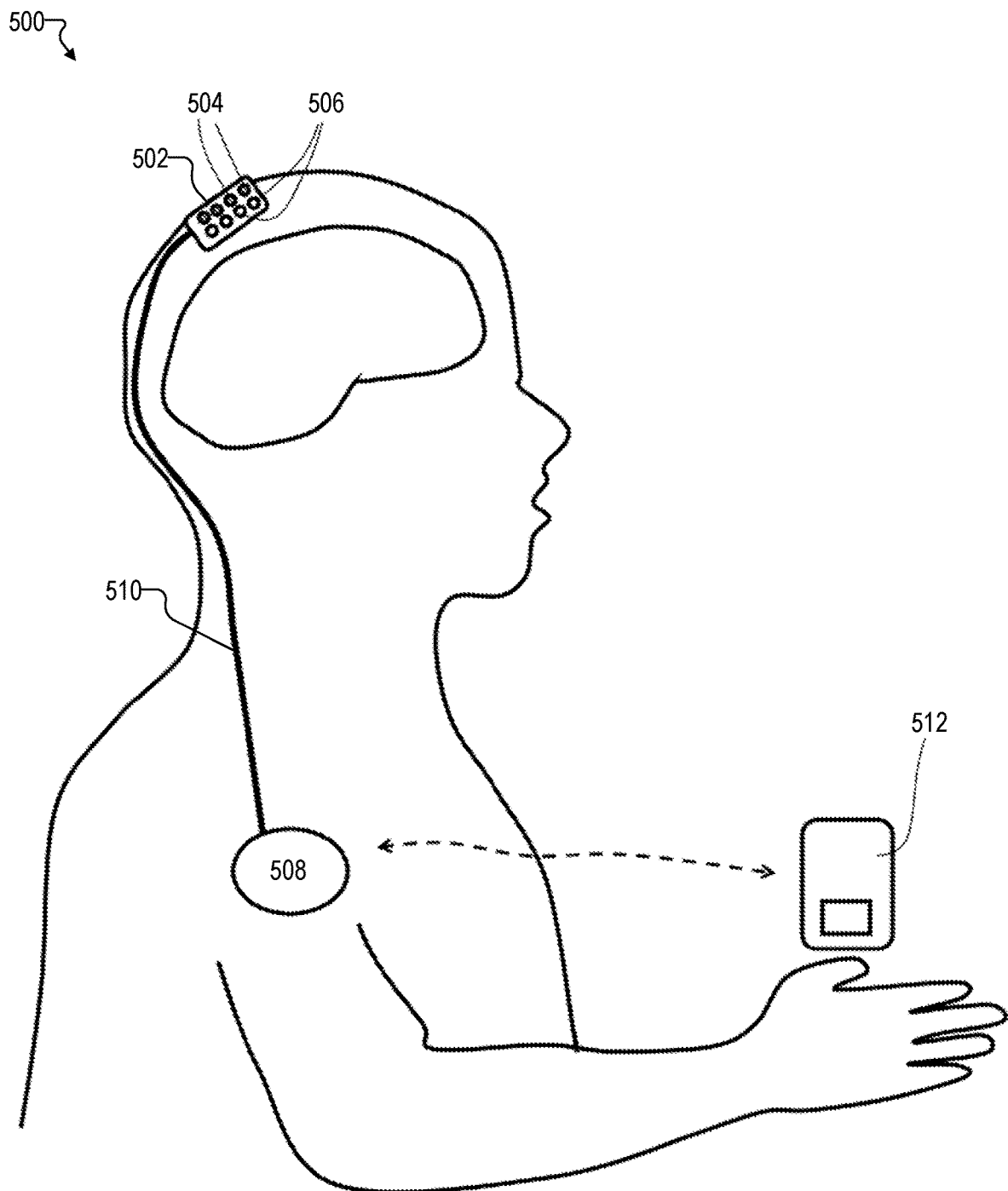
FIG. 5 illustrates an exemplary non-invasive wearable brain interface system.

FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be attached to and/or worn on a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described below in more detail and in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and/or for transforming photodetector measurements into an intensity value that represents an optical property of a target within the brain. Brain interface system 500 allows optical detection of deep anatomical locations beyond skin and bone (e.g., skull) by extracting data from photons originating from light sources 506 and emitted to a target location within the user's brain, in contrast to conventional imaging systems and methods (e.g., optical coherence tomography (OCT), continuous wave near infrared spectroscopy (CW-NIRS)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506. In some examples, processor 508 is implemented by or similar to processor 108 and/or controller 112.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). In some examples, remote processor 512 is implemented by or similar to processor 108 and/or controller 112.

Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detector 504 may be included elsewhere in brain interface system 500. For example, a light source may be included in processor 508 and/or in another wearable or non-wearable device and coupled to head mountable component 502 through an optical connection.

In some alternative embodiments, head mountable component 502 does not include individual detectors 504. Instead, one or more detectors configured to detect the scattered light from the target may be included elsewhere in brain interface system 500. For example, a detector may be included in processor 508 and/or in another wearable or non-wearable device and coupled to head mountable component 502 through an optical connection.

Figure 6:
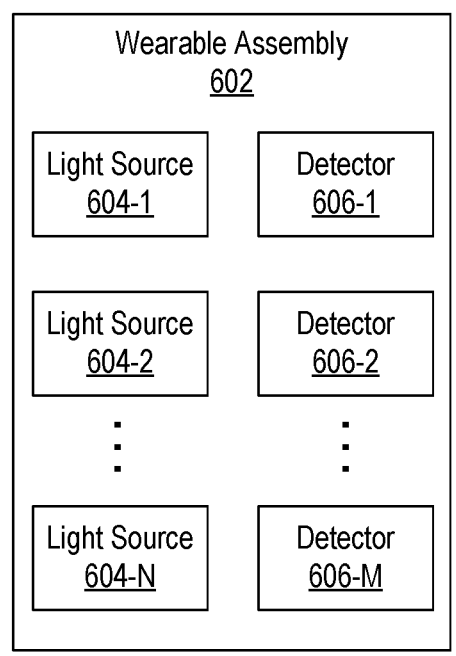
FIG. 6 illustrates an exemplary optical measurement system.

FIG. 6 shows an exemplary optical measurement system 600 in accordance with the principles described herein. Optical measurement system 600 may be an implementation of optical measurement system 100 and, as shown, includes a wearable assembly 602, which includes N light sources 604 (e.g., light sources 604-1 through 604-N) and M detectors 606 (e.g., detectors 606-1 through 606-M). Optical measurement system 600 may include any of the other components of optical measurement system 100 as may serve a particular implementation. N and M may each be any suitable value (i.e., there may be any number of light sources 604 and any number of detectors 606 included in optical measurement system 600 as may serve a particular implementation).

Light sources 604 are each configured to emit light (e.g., a sequence of light pulses) and may be implemented by any of the light sources described herein. Detectors 606 may each be configured to detect arrival times for photons of the light emitted by one or more light sources 604 after the light is scattered by the target. For example, a detector 606 may include a photodetector configured to generate a photodetector output pulse in response to detecting a photon of the light and a TDC configured to record a timestamp symbol in response to an occurrence of the photodetector output pulse, the timestamp symbol representative of an arrival time for the photon (i.e., when the photon is detected by the photodetector). Detectors 606 may be implemented by any of the detectors described herein.

Wearable assembly 602 may be implemented by any of the wearable devices, modular assemblies, and/or wearable units described herein. For example, wearable assembly 602 may be implemented by a wearable device (e.g., headgear) configured to be worn on a user's head. Wearable assembly 602 may additionally or alternatively be configured to be worn on any other part of a user's body.

Optical measurement system 600 may be modular in that one or more components of optical measurement system 600 may be removed, changed out, or otherwise modified as may serve a particular implementation. Additionally or alternatively, optical measurement system 600 may be modular such that one or more components of optical measurement system 600 may be housed in a separate housing (e.g., module) and/or may be movable relative to other components. Exemplary modular optical measurement systems are described in more detail in U.S. Provisional Patent Application No. 63/081,754, filed Sep. 22, 2020, U.S. Provisional Patent Application No. 63/038,459, filed Jun. 12, 2020, U.S. Provisional Patent Application No. 63/038,468, filed Jun. 12, 2020, U.S. Provisional Patent Application No. 63/038,481, filed Jun. 12, 2020, and U.S. Provisional Patent Application No. 63/064,688, filed Aug. 12, 2020, which applications are incorporated herein by reference in their respective entireties.

Figure 7:
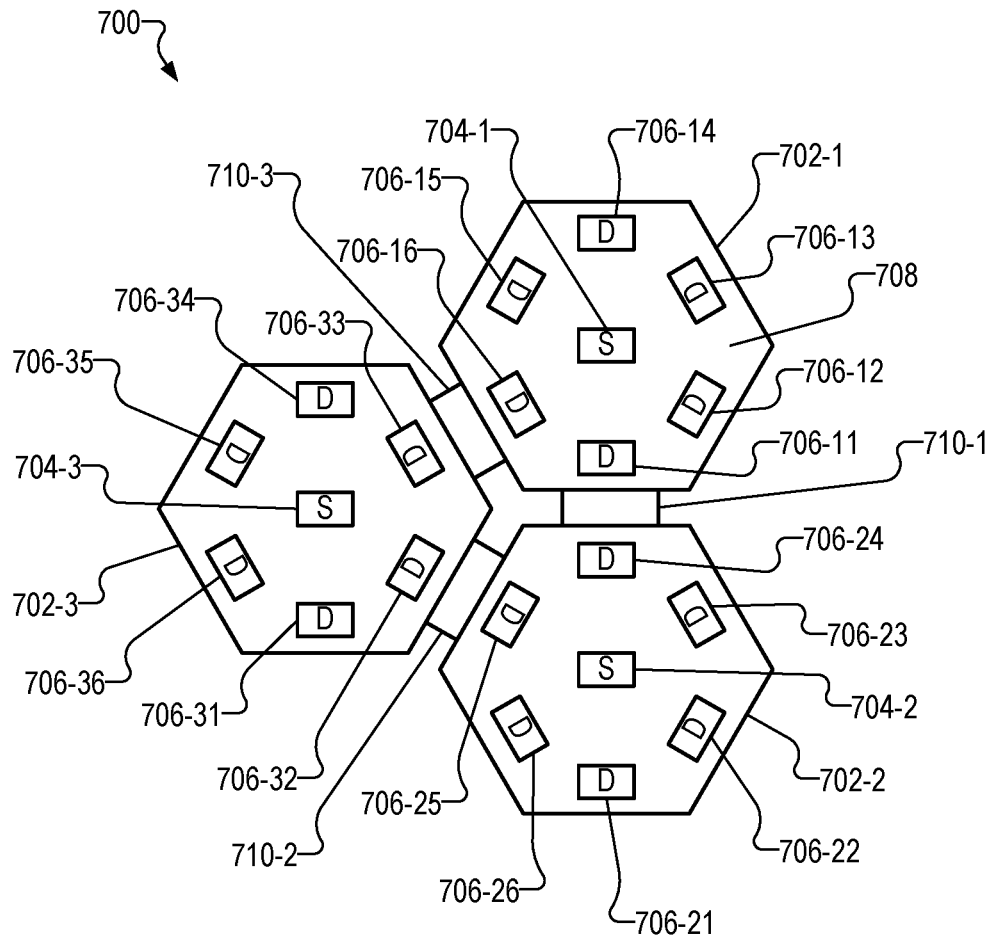
FIG. 7 illustrates an exemplary modular optical measurement system.

FIG. 7 illustrates an exemplary modular optical measurement system 700 that may implement optical measurement system 600. Optical measurement system 700 is illustrative of one of many different implementations of optical measurement system 600 that may be realized in accordance with the principles described herein.

As shown, optical measurement system 700 includes a plurality of wearable modules 702 (e.g., modules 702-1 through 702-3). Module 702-1 can represent or include a first module housing, module 702-2 can represent or include a separate second module housing, module 703-3 can represent or include a separate third module housing, and so forth. While three modules 702 are shown to be included in optical measurement system 700, in alternative configurations, any number of modules 702 (e.g., a single module up to sixteen or more modules) may be included in optical measurement system 700.

Each module 702 includes a light source 704 (e.g., light source 704-1 of module 702-1, light source 704-2 of module 702-2, and light source 704-3 of module 702-3) and a plurality of detectors 706 (e.g., detectors 706-11 through 706-16 of module 702-1, detectors 706-21 through 706-26 of module 702-2, and detectors 706-31 through 706-36 of module 702-3). In the particular implementation shown in FIG. 7, each module 702 includes a single light source 704 (labeled "S") and six detectors 706 (each labeled "D"). However, each module 702 may have any other number and arrangement of light sources 704 and detectors 706 as may serve a particular implementation. Any one or more components of a module 702 (e.g., a light source 704, detectors 706, and/or any other components) may be housed, in whole or in part, within a module housing.

Each light source 704 may be implemented by any light source described herein and may be configured to emit light directed at a target (e.g., the brain). Each light source 704 may also include any suitable optical components (e.g., an optical conduit) configured to guide and direct emitted light toward the target. Each light source 704 may be located at a center region of a surface 708 of the light source's corresponding module. For example, light source 704-1 is located at a center region of a surface 708 of module 702-1. In alternative implementations, a light source 704 of a module 702 may be located away from a center region of the module.

Each detector 706 may be implemented by any detector described herein and may include a plurality of photodetectors (e.g., SPADs) as well as other circuitry (e.g., TDCs). Each detector 706 may be configured to detect arrival times for photons of the light emitted by one or more light sources after the photons are scattered by the target. Each detector 706 may also include any suitable optical components (e.g., an optical conduit) configured to receive and guide photons scattered by the target toward the plurality of photodetectors included in the detector 706.

As shown in FIG. 7, the detectors 706 of a module 702 may be distributed around light source 704 of the same module 702. In this configuration, detectors 706 may be configured to detect photon arrival times for photons included in light pulses emitted by the light source 704 and scattered by the target. In some examples, the detectors 706 of a module 702 may all be equidistant from the light source 704 of the same module. Detectors 706 of a module 702 may be alternatively disposed on the module 702 in any other suitable way as may serve a particular implementation.

In some examples, the spacing between a light source 704 (e.g., a distal end portion of a light emitting optical conduit) and each detector 706 (e.g., a distal end portion of a light receiving optical conduit) is maintained at the same fixed distance on each module 702 to ensure homogeneous coverage over specific areas and to facilitate processing of the detected signals. The fixed spacing also provides consistent spatial (lateral and depth) resolution across the target area of interest, e.g., brain tissue. Moreover, maintaining a known distance between the light source and each detector allows subsequent processing of the detected signals to infer spatial (e.g., depth localization, inverse modeling) information about the detected signals.

As shown in FIG. 7, modules 702 are physically interconnected with one another in a modular wearable assembly. In some examples, the pose (e.g., position and/or orientation) of one or more modules 702 within the modular assembly is adjustable. With such configuration, the modular assembly can be adjusted to conform to a 3D (non-planar) surface, such as a user's head, and/or to target a specific region of interest (e.g., a specific region of the brain). Modules 702 may be adjustable in any suitable way. For example, as shown in FIG. 7 modules 702 are flexibly and/or movably interconnected to one another by connections 710 (e.g., connections 710-1 to 710-3) between adjacent modules 702. Connections 710 may be implemented by any suitable connecting mechanisms (e.g., ball joints, hinges, elastic bands, etc.) and/or support members (e.g., support frames, bands, rails, etc.). Exemplary adjustable modular assemblies are described in more detail in U.S. Provisional Patent Application No. 62/992,550, filed Mar. 20, 2020.

Additionally or alternatively, one or more modules 702 included in optical measurement system 700 may be physically unconnected from one or more other modules 702 and thus is adjustable relative to the other module(s) 702. For example, optical measurement system 700 may include a plurality of physically unconnected modular assemblies similar to the modular assembly illustrated in FIG. 7.

As shown in FIG. 7, modules 702 may have a hexagonal shape. Modules 702 may additionally or alternatively have any other suitable geometry (e.g., in the shape of a pentagon, octagon, square, rectangular, circular, triangular, free-form, etc.) as may serve a particular implementation.

In some configurations, one or more detectors 706 on a module 702 may be close enough to other light sources 704 on other modules 702 to detect photon arrival times for photons included in light pulses emitted by the other light sources 704. For example, detector 706-24 may detect photon arrival times for photons included in light pulses emitted by light source 704-1 (in addition to detecting photon arrival times for photons included in light pulses emitted by light source 704-2).

When optical measurement system 700 performs an optical measurement operation, a light source 704 (e.g., light source 704-1) directs a sequence of light pulses (e.g., laser pulses) toward the target. The light pulses may be short (e.g., 10-2000 picoseconds (ps)) and repeated at a high frequency (e.g., between 100,000 hertz (Hz) and 100 megahertz (MHz)). Photons in the emitted light pulses may be scattered by the target and detected by detectors 706. Optical measurement system 700 may measure a time relative to the light pulse for each detected photon. By counting the number of photons detected at each time relative to each light pulse repeated over a plurality of light pulses, optical measurement system 700 may generate a histogram that represents a light pulse response of the target (e.g., a temporal point spread function (TPSF)).

If the distance between the light source 704 and a detector 706 (the "source-detector distance") is known, the detected signal (e.g., TPSF) can be used to infer spatial information (e.g., depth localization) about the detected signals. As used herein, the source-detector distance refers to the linear distance between the point where a light pulse emitted by a light source 704 exits module 702 (i.e., a distal end (light-emitting) surface of a light-emitting optical conduit) and the point where photons included in the light pulse and scattered by the target enter module 702 (i.e., a distal end (light-receiving) surface of the light-receiving optical conduit).

As mentioned above, the position of a light source 704 on a module 702 and the detectors 706 on the same module 702 may be fixed. Thus, the source-detector distance between the light source 704 and each detector 706 on the same module 702 may be known. However, the source-detector distance between a light source 704 (e.g., light source 704-1) on a first module (e.g., module 702-1) and a detector (e.g., detector 706-24) on a second module (e.g., module 702-2) may not be known and may vary, such as due to manufacturing variations in the modules 702, flexing/bending of the modular assembly to conform to a 3D surface, and/or adjustment of the pose of one or more modules 702 relative to other modules 702. However, the source-detector distance between the light source 704 on the first module and the detector 706 on the second module can be estimated by a calibration process based on the signals detected by detectors 706, as will now be described.

Figure 8A:
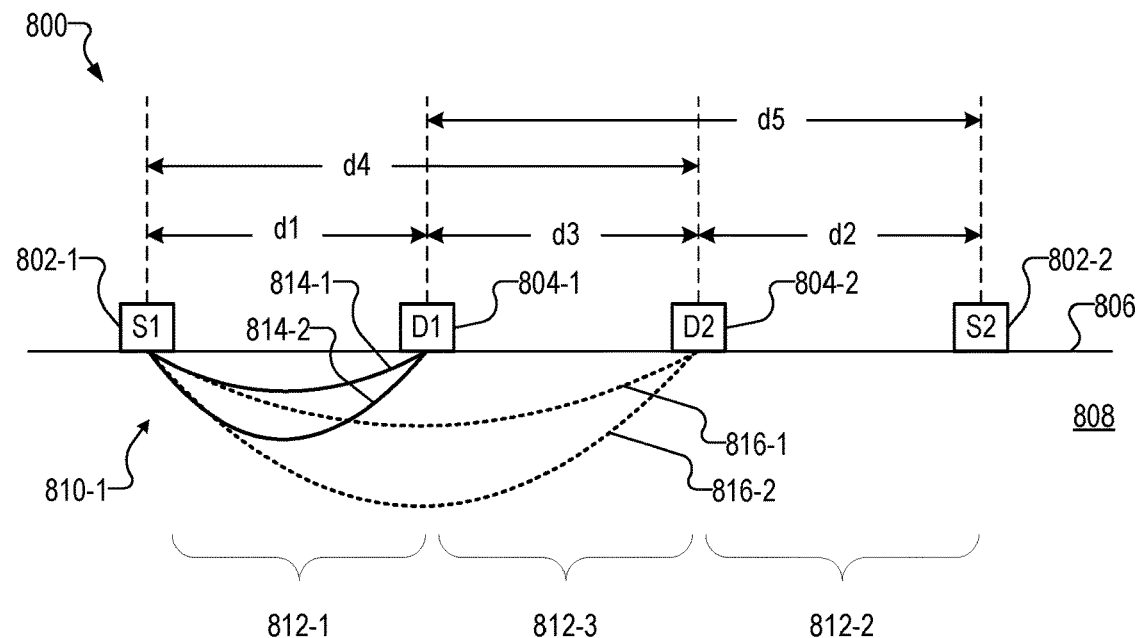
FIGS. 8A and 8B illustrate exemplary operations that may be performed by an exemplary optical measurement system during an exemplary calibration process.
Figure 8B:
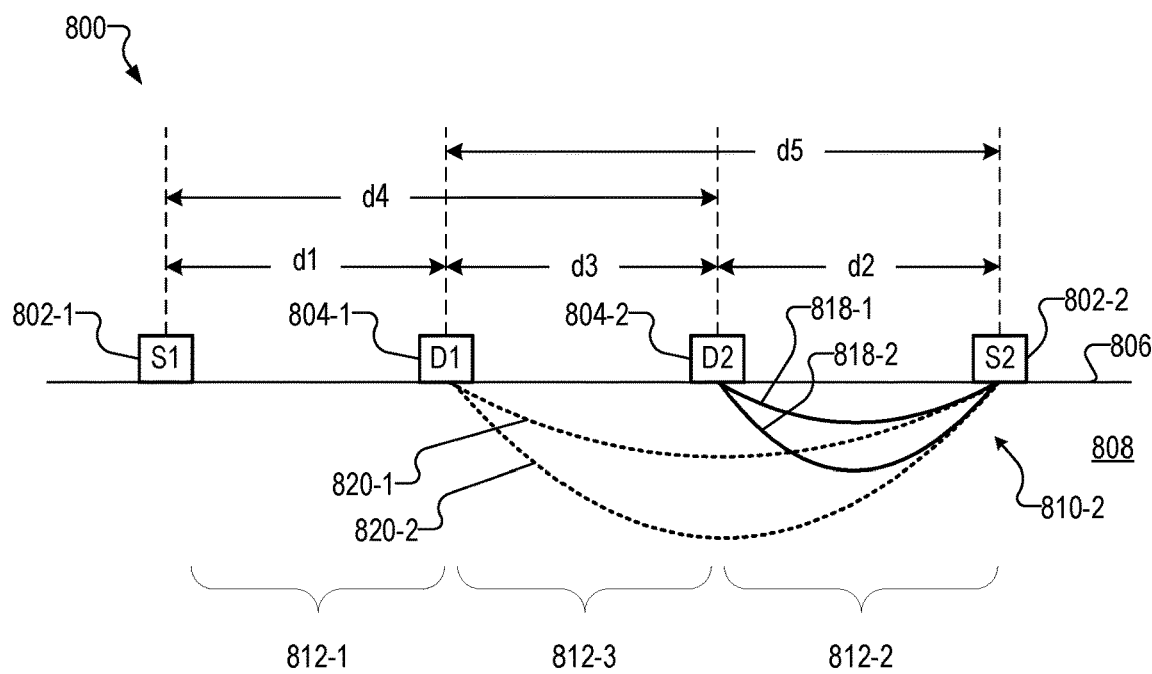

FIGS. 8A and 8B illustrate exemplary operations that may be performed by (or with) an exemplary optical measurement system 800 during a calibration process. Optical measurement system 800 may implement any optical measurement system described herein (e.g., optical measurement system 700). As shown, a first light source 802-1 (labeled "S1") (e.g., light source 704-1) and a first detector 804-1 (labeled "D1") (e.g., detector 706-11) are in contact with a surface 806 of a body of a user. A target 808 (e.g., the user's brain) is located beneath surface 806. A second light source 802-2 (labeled "S2") (e.g., light source 704-2) and a second detector 804-2 (labeled "D2") (e.g., light source 706-24) are also in contact with surface 806. First light source 802-1 is configured to emit a first light pulse 810-1 toward target 808, and second light source 802-2 is configured to emit a second light pulse 810-2 toward target 808. First detector 804-1 and second detector 804-2 are configured to detect photons included in first light pulse 810-1 and second light pulse 810-2 after the photons are scattered by target 808.

First detector 804-1 is separated from first light source 802-1 by a source-detector distance labeled d1, and second detector 804-2 is separated from second light source 802-2 by a source-detector distance labeled d2. First detector 804-1 and second detector 804-2 are separated by a distance labeled d3. Source-detector distance d1 and source-detector distance d2 may be known (e.g., from prior measurements, from module design and construction, etc.). In some examples, source-detector distance d1 and source-detector distance d2 are fixed, such as when the positions of light sources 802 and detectors 804 are fixed on their respective modules. On the other hand, distance d3 may be unknown, such as when a position of second light source 802-2 and second detector 804-2 are adjusted relative to a position of first light source 802-1 and first detector 804-1. Hence, a source-detector distance d4 between first light source 802-1 and second detector 804-2 (i.e., d1+d3) is unknown, as is a source-detector distance d5 between second light source 802-2 and first detector 804-1 (i.e., d2+d3). However, optical measurement system 800 is configured to determine source-detector distance d4 and source-detector distance d5 analytically as described herein.

The propagation of light through a turbid medium (e.g., the brain) may be modeled by a standard model of diffusion theory. In such models, the scattering of light in the target depends on, among other things, the source-detector distance and a parameter known as the reduced scattering coefficient $u'_s$, which represents the scattering probability of light per unit length together with an anisotropy factor. If the source-detector distance is known, the reduced scattering coefficient $u'_s$ of the target may be determined analytically from a detected TPSF by fitting the TPSF with a standard model of diffusion theory. On the other hand, if the reduced scattering coefficient $u'_s$ of the target is known, the source-detector distance can be calculated from the acquired TPSF and the model of diffusion theory. Optical measurement system 800 is configured to use this relationship to determine source-detector distance d4 and source-detector distance d5 based on a plurality of temporal distributions (TPSFs) of the photons included in light pulses 810 and detected by detectors 804.

In a first step of the calibration process, optical measurement system 800 may obtain calibration data (e.g., TPSFs from detectors 804 and first and second distances d1 and d2). Optical measurement system 800 may obtain calibration data in any suitable way, such as by generating the calibration data and/or by accessing previously generated calibrated stored data from memory or some other archived location.

FIG. 8A illustrates the generation, by optical measurement system 800, of TPSFs at a first time. As shown in FIG. 8A, optical measurement system 800 may direct first light source 802-1 to emit first light pulse 810-1 (which may be a sequence of light pulses) toward target 808 within the body of the user. First detector 804-1 may detect a first set of photons included in first light pulse 810-1 after the first set of photons are scattered by target 808 in a first region 812-1 of target 808. The first set of photons travel through first region 812-1 in a possible optical path represented by the area between solid banana path lines 814-1 and 814-2. Second detector 804-2 may detect a second set of photons included in first light pulse 810-1 after the second set of photons are scattered by target 808 in first region 812-1 and a third region 812-3 of target 808. The second set of photons travel through first region 812-1 and third region 812-3 in a possible optical path represented by the area between dashed banana path lines 816-1 and 816-2.

Optical measurement system 800 may determine a first temporal distribution (TPSF) of the first set of photons included in first light pulse 810-1 and detected by first detector 804-1. Optical measurement system 800 may also determine a second temporal distribution (TPSF) of the second set of photons included in first light pulse 810-1 and detected by second detector 804-2. Optical measurement system 800 may determine the first temporal distribution and the second temporal distribution in any suitable way, including in any way described herein.

FIG. 8B illustrates the generation, by optical measurement system 800, of TPSFs at a second time that is subsequent to (or prior to) the first time illustrated in FIG. 8A. As shown in FIG. 8B, optical measurement system 800 may direct second light source 802-2 to emit second light pulse 810-2 (which may be a sequence of light pulses) toward target 808 within the body of the user. Second detector 804-2 may detect a third set of photons included in second light pulse 810-2 after the third set of photons are scattered by target 808 in a second region 812-2 of target 808. The third set of photons travel through second region 812-2 in a possible optical path represented by the area between solid banana path lines 818-1 and 818-2. First detector 804-1 may detect a fourth set photons included in second light pulse 810-2 after the fourth set of photons are scattered by target 808 in second region 812-2 and third region 812-3 of target 808. The fourth set of photons travel through second region 812-2 and third region 812-3 in a possible optical path represented by the area between dashed banana path lines 820-1 and 820-2.

Optical measurement system 800 may determine a third temporal distribution (TPSF) of the third set of photons included in second light pulse 810-2 and detected by second detector 804-2. Optical measurement system 800 may also determine a fourth temporal distribution (TPSF) of the fourth set of photons included in second light pulse 810-2 and detected by first detector 804-1. Optical measurement system 800 may determine the third temporal distribution and the fourth temporal distribution in any suitable way, including in any way described herein.

Optical measurement system 800 may also obtain values of source-detector distance d1 and source-detector distance d2. When d1 and d2 are known, optical measurement system 800 may use the first, second, third, and fourth temporal distributions (obtained as described above) to determine source-detector distance d4 and source-detector distance d5, as will be described below in more detail. Optical measurement system 800 may obtain source-detector distance d1 and source-detector distance d2 in any suitable way. As mentioned, d1 and d2 may be known. For example, first light source 802-1 and first detector 804-1 may be included in a first wearable module and positioned within the first wearable module at a fixed distance. Similarly, second light source 802-2 and second detector 804-2 may be included in a second wearable module and positioned within the second wearable module at a fixed distance. In some examples, the first wearable module and the second wearable module each includes memory that stores data (e.g., distance data, model information data, serial number data, etc.) that may be accessed by optical measurement system 800 and used to determine source-detector distance d1 and source-detector distance d2. In some examples, optical measurement system 800 may use the stored data (e.g., serial number data) to obtain source-detector distance d1 and source-detector distance d2 from a remote computing device (e.g., a remote server, etc.).

Additionally or alternatively, source-detector distance d1 and source-detector distance d2 may be provided to optical measurement system 800 by user input. For example, the position of one or more light sources 802 and/or detectors 804 may be adjustable, and the user may then measure or determine source-detector distance d1 and/or source-detector distance d2 and provide that information to optical measurement system 800.

In the second step of the calibration process, optical measurement system 800 may use the calibration data to determine reduced scattering coefficients u'$_s$ of target 808. For example, optical measurement system 800 may determine, based on the first temporal distribution and source-detector distance d1, a first reduced scattering coefficient u'$_{s1}$ of target 808 within first region 812-1. Optical measurement system 800 may also determine, based on the second temporal distribution and source-detector distance d2, a second reduced scattering coefficient u'$_{s2}$ of target 808 within second region 812-2. Optical measurement system 800 may determine first reduced scattering coefficient u'$_{s1}$ and second reduced scattering coefficient u'$_{s2}$ in any suitable way. For example, optical measurement system 800 may fit the first temporal distribution and the third temporal distribution to a standard model of diffusion theory and, based on the known values of source-detector distances d1 and d2, directly calculate first reduced scattering coefficient u'$_{s1}$ and second reduced scattering coefficient u'$_{s2}$.

In the third step of the calibration process, optical measurement system 800 may determine source-detector distance d4 and source-detector distance d5 based on the obtained calibration data and the calculated first reduced scattering coefficient u'$_{s1}$ and second reduced scattering coefficient u'$_{s2}$. The optical path of the second set of photons through target 808 has the previously calculated first reduced scattering coefficient u'$_{s1}$ as well as the unknown third reduced scattering coefficient u'$_{s3}$, and the optical path of the fourth set of photons through target 808 has the previously calculated second reduced scattering coefficient u'$_{s2}$ as well as the unknown third reduced scattering coefficient u'$_{s3}$. Thus, there exist two unknown values: third distance d3 and third reduced scattering coefficient u'$_{s3}$ of target 808 in third region 812-3. These two unknown values may be resolved by fitting two different measurements—the second temporal distribution and the fourth temporal distribution—to the standard model of diffusion theory. Once third distance d3 is determined, source-detector distance d4 (i.e., d1+d3) and source-detector distance d5 (i.e., d2+d3) may be easily calculated.

Various modifications may be made to the embodiments described above. For example, where first reduced scattering coefficient µ'$_{s1}$ and second reduced scattering coefficient µ'$_{s2}$ are identical (or within a predetermined tolerance), optical measurement system 800 may assume that third reduced scattering coefficient µ'$_{s3}$ is also the same. Accordingly, source-detector distance d4 may be determined directly from the second temporal distribution and the first reduced scattering coefficient µ'$_{s1}$ (or third reduced scattering coefficient µ'$_{s3}$). Similarly, source-detector distance d5 may be determined directly from the fourth temporal distribution and the second reduced scattering coefficient µ'$_{s2}$ (or third reduced scattering coefficient µ'$_{s3}$).

The calibration process described above may be performed with a single wavelength of light. That is, first light pulse 810-1 and second light pulse 810-2 have the same wavelength (e.g., 650 nm). In some examples, optical measurement system 800 may repeat the calibration process with one or more additional wavelengths (e.g., 810 nm). The reduced scattering coefficient u'$_s$ of target 808 is wavelength dependent, and thus target 808 will have different values of first, second, and third reduced scattering coefficients u'$_{s1}$, u'$_{s2}$, and u'$_{s3}$ for each different wavelength. However, the source-detector distance d4 and source-detector distance d5 should be the same, so the results of the calibration process with the additional wavelengths can be used to validate, correct, or average the calibration with the first wavelength.

To illustrate, optical measurement system 800 may direct first light source 802-1 to also emit a third light pulse (not shown) toward target 808 and may direct second light source 802-2 to also emit a fourth light pulse (not shown) toward target 808. First light pulse 810-1 and second light pulse 810-2 may have a first wavelength (e.g., 650 nm), and the third and fourth light pulses may have a second wavelength (e.g., 810 nm) that is different from the first wavelength.

Optical measurement system 800 may determine a plurality of additional temporal distributions of additional photons detected by first detector 804-1 and second detector 804-2 and included in the third light pulse and the fourth light pulse. Optical measurement system 800 may determine, based on the plurality of additional temporal distributions of additional photons, source-detector distance d4 and source-detector distance d5. In some examples, optical measurement system 800 may confirm or validate the calculated source-detector distances d4 and d5 of the first calibration process if the result of the second calibration process matches or is within a predetermined tolerance (e.g., a predetermined amount or a predetermined percentage) of the result of the first calibration process.

In the examples described above, optical measurement system 800 may determine the source-detector distance between a light source (e.g., light source 704-1) on a first wearable module (e.g., wearable module 702-1) and a detector (e.g., detector 706-24) on a second wearable module (e.g., wearable module 704-2). In some examples, one or more additional detectors (e.g., detector 706-33) on the second or other wearable modules (e.g., wearable module 704-3) separate from the first wearable module may also be close enough to the light source to detect photons from light pulses emitted by the light source and scattered by the target. Accordingly, optical measurement system 800 may be configured to perform the calibration process described above to determine the source-detector distance between the light source (e.g., light source 704-1) on the first wearable module (e.g., wearable module 702-1) and a plurality of detectors (e.g., detectors 706-24 and 706-34) on one or more different wearable modules (e.g., wearable modules 702-2 and 702-3). Additionally, optical measurement system 800 may be configured to perform this calibration process for each of a plurality of wearable modules and/or light sources. To perform such calibration on a plurality of wearable modules and/or light sources, optical measurement system 800 may time-multiplex the calibration process (e.g., the emission of light pulses from light sources) so that each detector detects photons from only one light source at a time.

In some examples, first detector 804-1 and second detector 804-2 are positioned substantially inline with first light source 802-1 and second light source 802-2. With such configuration, the third set of photons and the fourth set of photons both pass through the same third region 812-3. This configuration is illustrated with reference to FIG. 7, which shows that detector 706-11 (which may implement first detector 804-1) and detector 706-24 (which may implement second detector 804-2) are positioned on an imaginary straight line connecting light source 704-1 (which may implement first light source 802-1) and light source 704-2 (which may implement second light source 802-2).

In alternative examples, a detector 706 is not positioned inline with a first light source and a second light source. For example, as shown in FIG. 7, detector 706-25 is not inline with sources 704-1 and 704-2. However, detector 706-25 may be close enough to light source 704-1 to detect photons from light pulses emitted by light source 704-1. To determine the source-detector distance between light source 704-1 and detector 706-25, a different or modified calibration process may be performed, as illustrated in FIG. 9.

Figure 9:
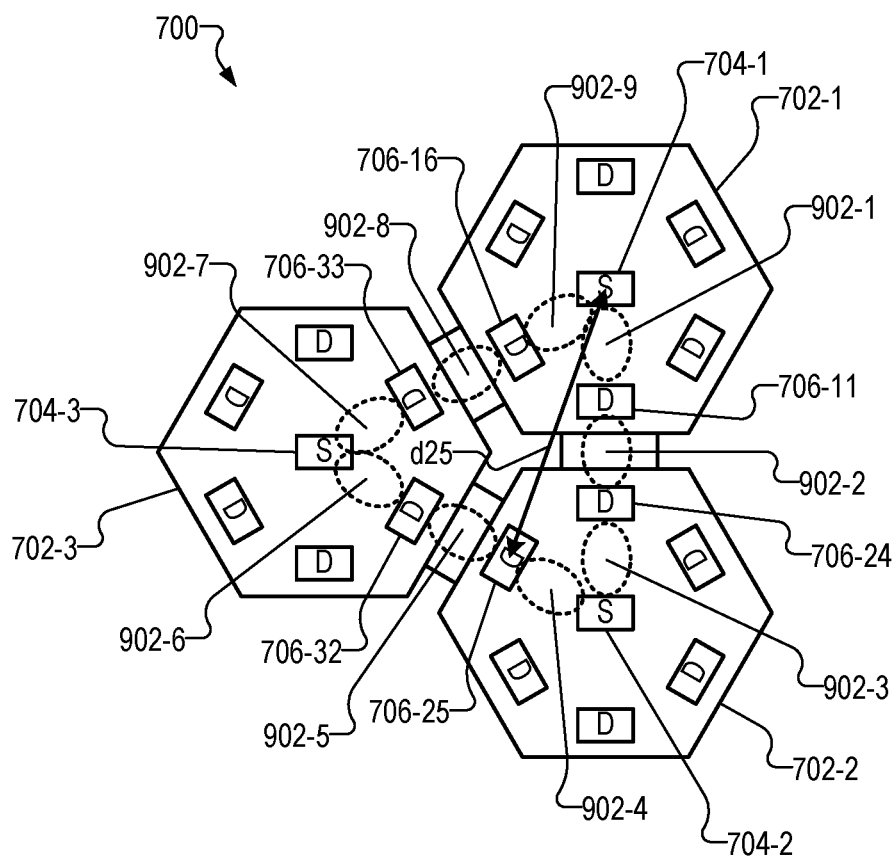
FIG. 9 illustrates the modular optical measurement system of FIG. 7 as used to determine a distance between a light source and a detector.

FIG. 9 shows optical measurement system 700 (certain reference numerals have been omitted for purposes of this discussion). To determine the source-detector distance between light source 704-1 and detector 706-25 (indicated by the arrow-line labeled "d25"), optical measurement system 700 may estimate the reduced scattering coefficient $\mu'_{sD25}$ of the target in the region between light source 704-1 and detector 706-25 and use a standard model of diffusion theory to determine, based on the estimated reduced scattering coefficient $\mu'_{sD25}$, the unknown source-detector distance d25. The reduced scattering coefficient $\mu'_{sD25}$ may be estimated in any suitable way.

In some examples, the reduced scattering coefficient $\mu'_{sD25}$ may be estimated based on the known reduced scattering coefficient $\mu'_s$ in adjacent or nearby regions of the target. FIG. 9 shows a plurality of dashed-line ovals representing regions 902 (e.g., regions 902-1 through 902-9) of the target for which the reduced scattering coefficient $\mu'_s$ (e.g., $\mu'_{s1}$, $\mu'_{s2}$, and $\mu'_{s3}$) was previously determined by the calibration process described above for inline detectors 706. In some examples, the reduced scattering coefficient $\mu'_s$ in a plurality of regions (e.g., regions 902-1 through 902-3) may be extended or extrapolated to the region between detector 704-1 and detector 706-25. Additionally or alternatively, optical measurement system 700 may generate, based on the reduced scattering coefficients $\mu'_s$ in each of regions 902-1 through 902-9, a gradient map of the reduced scattering coefficient $\mu'_s$ within the entire region bounded by regions 902-1 through 902-9. In some examples, the estimation of the reduced scattering coefficient $\mu'_{sD25}$ may be conditioned on satisfaction of certain criteria (e.g., the variation in the reduced scattering coefficients $\mu'_s$ in adjacent regions is less than or equal to a predetermined maximum value, etc.).

In the examples described above, the source-detector distance between a light source and a detector may be determined based on a plurality of temporal distributions obtained from the detection, by two different detectors, of light pulses emitted from two different light sources but having the same wavelength. In alternative embodiments, as will be illustrated with reference to FIGS. 10A-12, the source-detector distance between a light source and a detector may be determined based on a plurality of temporal distributions obtained from the detection, by the detector, of light pulses from the light source in two or more wavelengths.

Figure 10A:
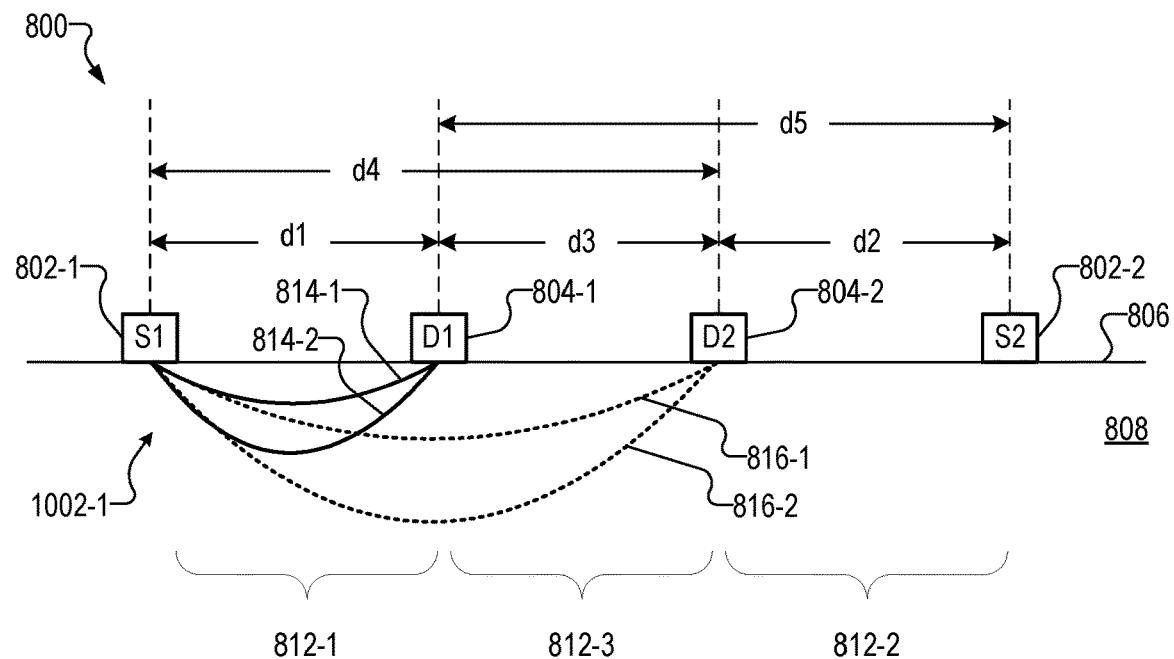
FIGS. 10A and 10B illustrate exemplary operations that may be performed by an optical measurement system during another exemplary calibration process.
Figure 10B:
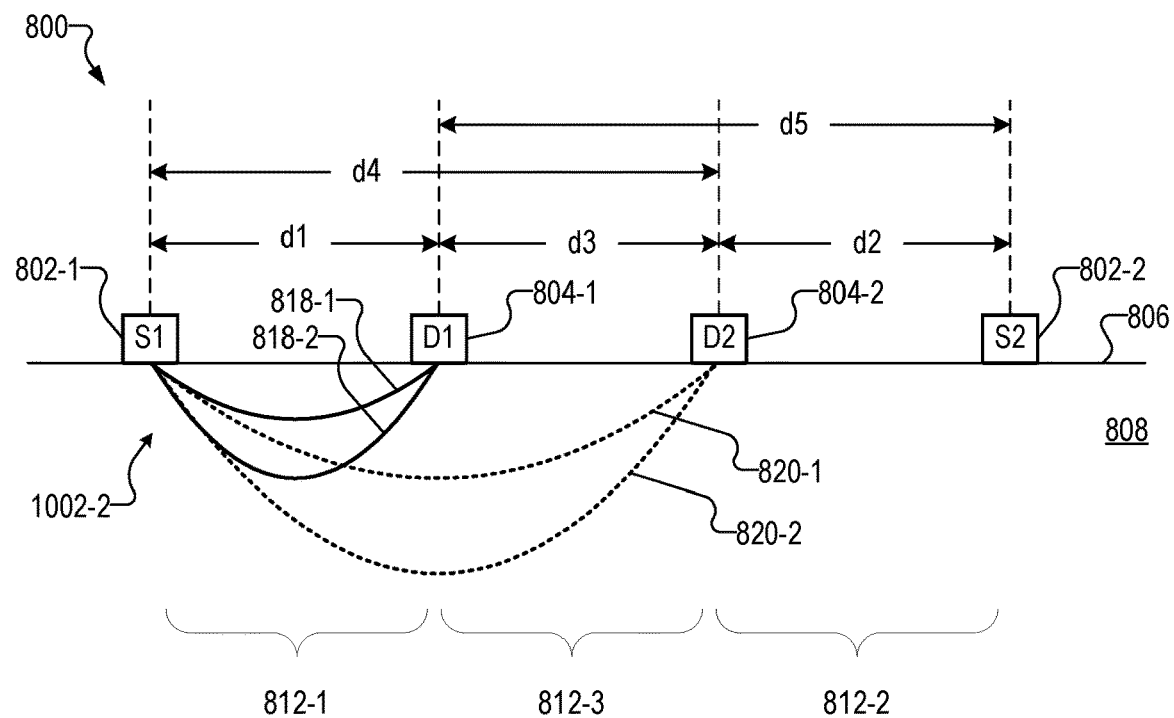

FIGS. 10A and 10B illustrate exemplary operations that may be performed by (or with) optical measurement system 800 during another exemplary calibration process to determine source-detector distance d4. It will be understood that the same calibration process may also be performed to determine source-detector distance d5. In a first step of the calibration process, optical measurement system 800 may obtain calibration data (e.g., TPSFs) from first detector 804-1. Optical measurement system 800 may obtain the calibration data in any suitable way, such as by generating the calibration data and/or by accessing previously generated calibrated data from memory or some other location.

FIG. 10A illustrates the generation, by optical measurement system 800, of TPSFs from first detector 804-1 and second detector 804-2 at a first time. As shown in FIG. 10A, optical measurement system 800 may direct first light source 802-1 to emit a first light pulse 1002-1 (which may be a sequence of light pulses) toward target 808 within the body of the user. First light pulse 1002-1 has a first wavelength (e.g., 650 nm). First detector 804-1 may detect a first set of photons included in first light pulse 1002-1 after the first set of photons are scattered by target 808 in first region 812-1. The first set of photons travel through first region 812-1 in a possible optical path represented by the area between solid banana path lines 814-1 and 814-2. Second detector 804-2 may detect a second set of photons included in first light pulse 1002-1 after the second set of photons are scattered by target 808 in first region 812-1 and third region 812-3. The second set of photons travel through first region 812-1 and third region 812-3 in a possible optical path represented by the area between dashed banana path lines 816-1 and 816-2.

Optical measurement system 800 may determine a first temporal distribution (TPSF) of the first set of photons included in first light pulse 1002-1 and detected by first detector 804-1. Optical measurement system 800 may also determine a second temporal distribution (TPSF) of the second set of photons included in first light pulse 1002-1 and detected by second detector 804-2. Optical measurement system 800 may determine the first temporal distribution and the second temporal distribution in any suitable way, including in any way described herein.

FIG. 10B illustrates the generation, by optical measurement system 800, of TPSFs from first detector 804-1 and second detector 804-2 at a second time that is subsequent to (or prior to) the first time illustrated in FIG. 10A. As shown in FIG. 10B, optical measurement system 800 may direct first light source 802-1 to emit a second light pulse 1002-2 (which may be a sequence of light pulses) toward target 808 within the body of the user. Second light pulse 1002-2 has a second wavelength (e.g., 850 nm) that is different from the first wavelength. First detector 804-1 may detect a third set of photons included in second light pulse 1002-2 after the third set of photons are scattered by target 808 in first region 812-1. The third set of photons travel through first region 812-1 in a possible optical path represented by the area between solid banana path lines 818-1 and 818-2. Second detector 804-2 may detect a fourth set of photons included in second light pulse 1002-2 after the fourth set of photons are scattered by target 808 in first region 812-1 and third region 812-3. The fourth set of photons travel through first region 812-1 and third region 812-3 in a possible optical path represented by the area between dashed banana path lines 820-1 and 820-2.

Optical measurement system 800 may determine a third temporal distribution (TPSF) of the third set of photons included in second light pulse 1002-2 and detected by first detector 804-1. Optical measurement system 800 may also determine a fourth temporal distribution (TPSF) of the fourth set of photons included in second light pulse 1002-2 and detected by second detector 804-2. Optical measurement system 800 may determine the third temporal distribution and the fourth temporal distribution in any suitable way, including in any way described herein.

Figure 11A:
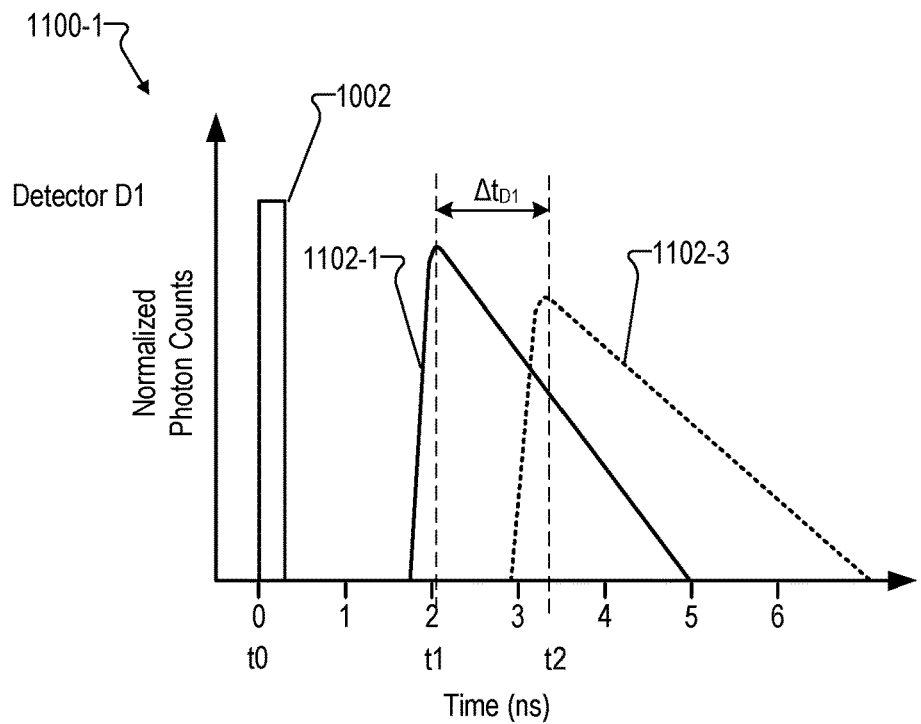
FIGS. 11A and 11B illustrate detection signals from a first detector and a second detector.
Figure 11B:
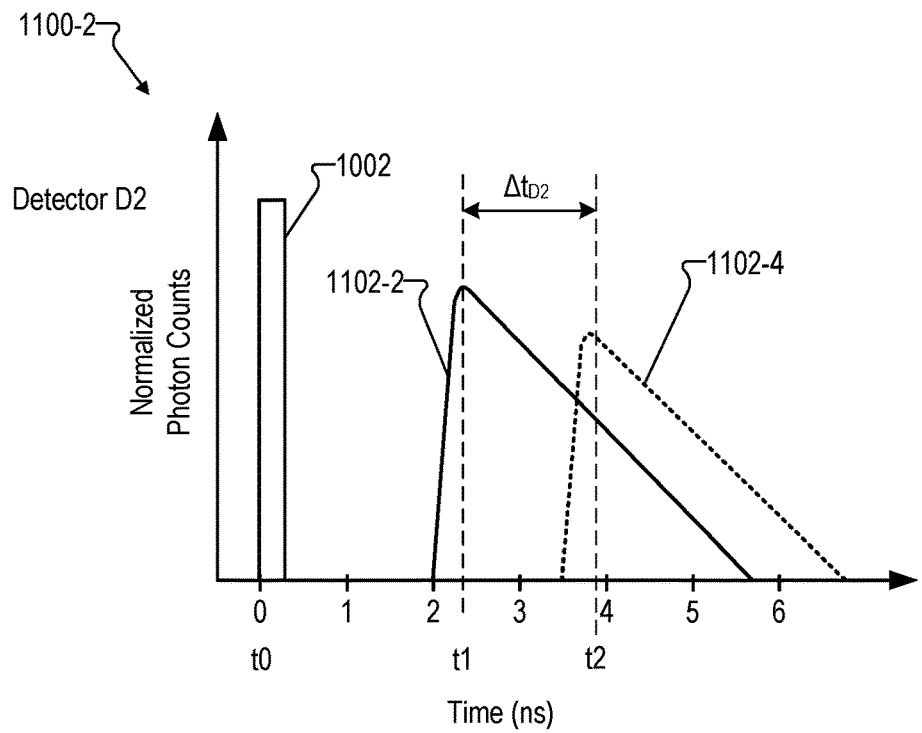

Target 808 (e.g., biological tissue) scatters different wavelengths of light differently, and the distance between light source 802-1 and detectors 804 affects the intensity and time-of-flight of the photons included in first light pulse 1002-1 and second light pulse 1002-2 and detected by detectors 804. For example, FIG. 11A illustrates a graph 1100-1 showing the detection signals from first detector 804-1, and FIG. 11B illustrates a graph 1100-2 showing the detection signals from second detector 804-2. As shown in FIG. 11A, the detection signals from first detector 804-1 includes a first TPSF 1102-1 representing the first temporal distribution (generated from light having the first wavelength) relative to first light pulse 1002-1 and a third TPSF 1102-3 representing the third temporal distribution (generated from light having the second wavelength) relative to second light pulse 1002-2. Light pulses 1002 have been normalized to an initial time t0. The peak of first TPSF 1102-1 occurs at time t1, and the peak of third TPSF 1102-3 occurs at time t2. The distance $\Delta t_{D1}$ between the peaks of TPSF 1102-1 and 1102-3 (e.g., between time t2 and time t1) along the time-axis is related (at least in part) to the source-detector distance d1 (i.e., the distance between first light source 802-1 and first detector 804-1).

Similarly, as shown in FIG. 11B, the detection signals from second detector 804-2 includes a second TPSF 1102-2 representing the second temporal distribution (generated from light having the first wavelength) relative to first light pulse 1002-1 and a fourth TPSF 1102-4 representing the fourth temporal distribution (generated from light having the second wavelength) relative to second light pulse 1002-2. Light pulses 1002 have been normalized to an initial time t0. The peak of second TPSF 1102-2 occurs at time t1, and the peak of fourth TPSF 1102-4 occurs at time t2. The distance $\Delta t_{D2}$ between the peaks of TPSF 1102-2 and 1102-4 (e.g., between time t2 and time t1) along the time-axis is related (at least in part) to the source-detector distance d4 (i.e., the distance between first light source 802-1 and second detector 804-2).

Figure 12:
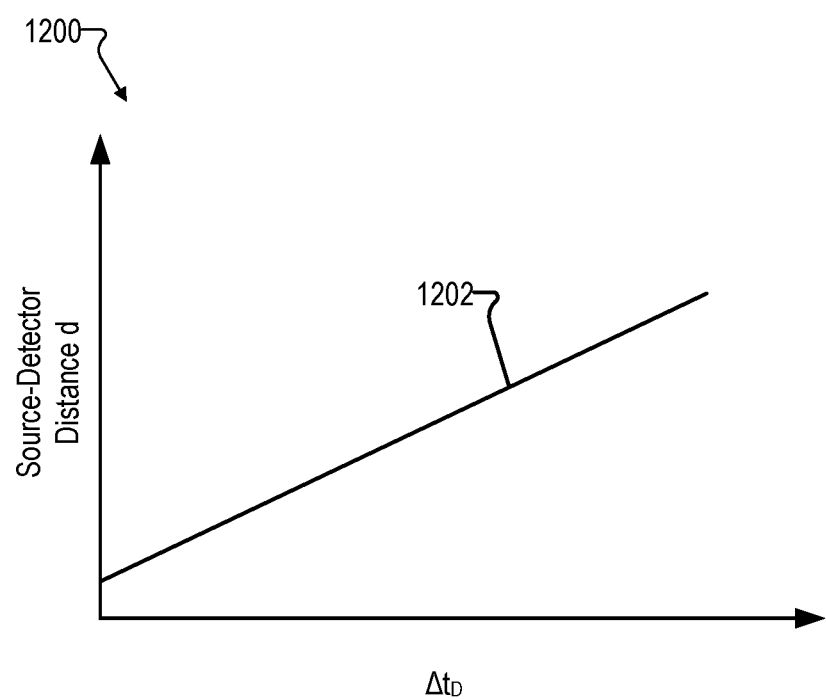
FIG. 12 illustrates an exemplary model representative of a possible relationship between a source-detector distance and the distance between peaks of two temporal distributions of photons measured at different wavelengths by a single detector.

Based on the wavelength-dependence of peak photon arrival times at a detector, a model can be generated and used to determine, based on the detection signal of second detector 804-2, the source-detector distance d4. FIG. 12 illustrates an exemplary model 1200 representative of a possible relationship between a source-detector distance and the distance between peaks of two TPSFs measured at different wavelengths by a single detector. The x-axis represents the time difference $\Delta t_D$ between the peaks of TPSFs measured at different wavelengths by a detector relative to a normalized light pulse, and the y-axis represents the source-detector distance d. As shown in FIG. 12, a curve 1202 representing the relationship between $\Delta t_D$ and d is linear. However, it will be appreciated that curve 1202 may have any other form based on physical conditions, instrument properties, etc. In some examples, $\Delta t_D$ may be measured at various values of source-detector distance, and a source-detector distance estimation model may be generated based on a regression analysis of the measurement data.

In some examples, the source-detector distance (e.g., the distance between peaks of TPSFs of different wavelengths) may also be related to one or more other parameters, such as the absolute distance of a TPSF peak from the light pulse 1002 (e.g., the difference between time t1 and time t0 or the difference between time t2 and time t0), the wavelengths used, TPSF peak intensity, difference in peak intensity, light pulse intensity, tissue type, tissue properties (e.g., tissue oxygenation, saturation, etc.), etc. Such additional parameters may also be included in the source-detector distance estimation model.

In some examples, the source-detector distance estimation model may be generated in real-time (e.g., in operation while worn by the user) during the calibration process. For example, $\Delta t_D$ for various source-detector distances for inline detectors 706 may be measured in accordance with the calibration process described above, and this data may then be used to generate a source-detector distance estimation model that may be used to determine source-detector distances for detectors that are not inline with multiple light sources. Additionally or alternatively, the source-detector distance estimation model may be generated prior to performing the calibration process and/or prior to the user using the optical measurement system. Data representative of the source-detector distance estimation model may be stored by optical measurement system 1000, or may otherwise be stored remotely from optical measurement system 1000 and accessible by optical measurement system 1000 during the calibration process.

Returning again to FIGS. 10A and 10B, optical measurement system 1000 may determine the source-detector distance d4 based on the obtained calibration data and a source-detector distance estimation model. For example, optical measurement system 800 may apply the second temporal distribution and the fourth temporal distribution (obtained from second detector 804-2) as inputs to the source-detector distance estimation model to determine the source-detector distance d4. In some examples, optical measurement system 800 may confirm the estimated source-detector distance d4 by applying the first temporal distribution and the third temporal distribution (obtained from first detector 804-1) as inputs to the source-detector distance estimation model to estimate the source-detector distance d1 and comparing the estimated source-detector distance d1 with a known value of source-detector distance d1. If the estimated value matches (or is within a predetermined tolerance) of the known value of d1, optical measurement system may confirm the source-detector distance d4.

Figure 13A:
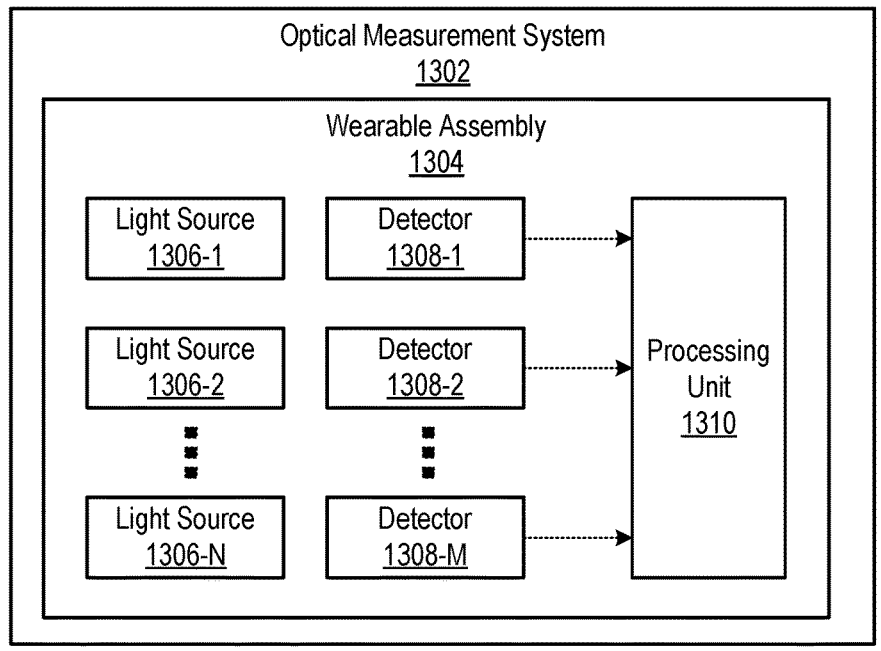
FIGS. 13A and 13B illustrate exemplary configurations of an exemplary optical measurement system that includes a processing unit.
Figure 13B:
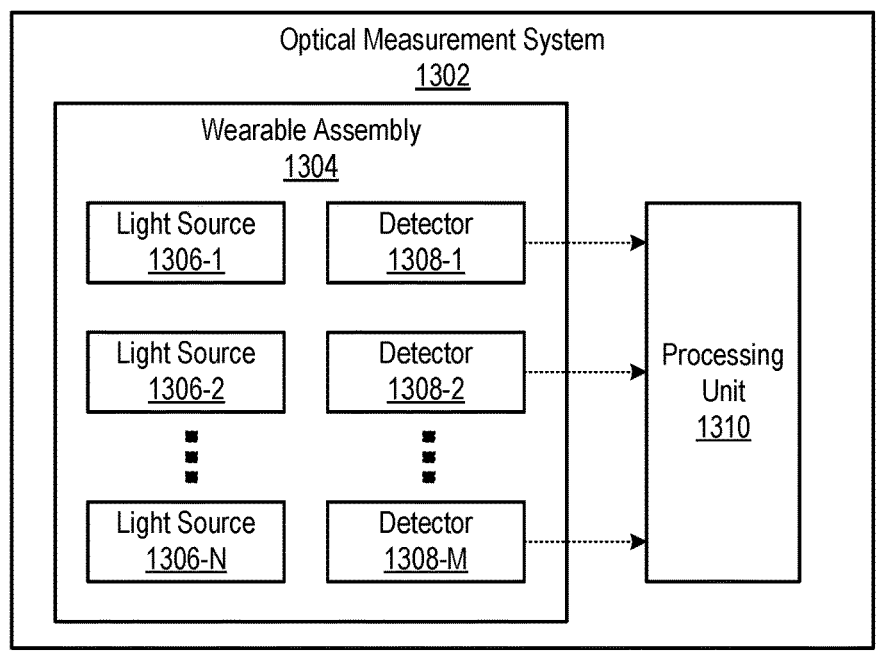

In some examples, the optical measurement systems described herein (e.g., optical measurement system 100, 700, or 800) may further include a processing unit configured to perform one or more operations based on photon arrival times detected by the detectors described herein. For example, FIGS. 13A-13B show illustrative configurations 1300-1 and 1300-2 of an exemplary optical measurement system 1302 in accordance with the principles described herein.

Optical measurement system 1302 may be an implementation of optical measurement system 100, 700, or 800 and, as shown, includes a wearable assembly 1304, which includes N light sources 1306 (e.g., light sources 1306-1 through 1306-N) and M detectors 1308 (e.g., detectors 1308-1 through 1308-M). Optical measurement system 1302 may include any of other components as may serve a particular implementation.

Wearable assembly 1304 may be implemented by any of the wearable devices, wearable modules, and/or wearable units described herein (e.g., wearable assembly 602). For example, wearable assembly 1304 may be implemented by a wearable device configured to be worn on a user's head. Wearable assembly 1304 may additionally or alternatively be configured to be worn on any other part of a user's body. In some examples, optical measurement system 1302 may include a plurality of wearable assemblies 1304.

Light sources 1306 are each configured to emit light and may be implemented by any of the light sources described herein. Detectors 1308 may each be configured to detect arrival times for photons of the light emitted by one or more light sources 1306 after the light is scattered by the target or diverted without being scattered by the target. For example, a detector 1308 may include a photodetector configured to generate a photodetector output pulse in response to detecting a photon of the light and a TDC configured to record a timestamp symbol in response to an occurrence of the photodetector output pulse, the timestamp symbol representative of an arrival time for the photon. Detectors 1308 may be implemented by any of the detectors described herein.

In configuration 1300-1, a processing unit 1310 is also included in wearable assembly 1304. In configuration 1300-2, processing unit 1310 is not included in wearable assembly 1304 (i.e., processing unit 1310 is located external to wearable assembly 1304). Either configuration 1300-1 or 1300-2 may be used in accordance with the systems, circuits, and methods described herein.

Detectors 1308 on wearable assembly 1304 may output signals representative of photon arrivals, as described herein. Processing unit 1310 is configured to receive the output signals and perform one or more operations based on the signals. For example, processing unit 1310 may generate measurement data (e.g., one or more histograms) based on the signals, as described herein.

As mentioned, in configuration 1300-2, processing unit 1310 is not included in wearable assembly 1304. For example, processing unit 1310 may be included in a wearable device separate from wearable assembly 1304. To illustrate, processing unit 1310 may be included in a wearable device configured to be worn off the head (e.g., on a belt) while wearable assembly 1304 is worn on the head. In these examples, one or more communication interfaces (e.g., cables, wireless interfaces, etc.) may be used to facilitate communication between wearable assembly 1304 and the separate wearable device.

Additionally or alternatively, in configuration 1300-2, processing unit 1310 may be remote from the user (i.e., not worn by the user). For example, processing unit 1310 may be implemented by a stand-alone computing device communicatively coupled to wearable assembly 1304 by way of one or more communication interfaces (e.g., cables, wireless interfaces, etc.).

In some examples, processing unit 1310 may be distributed between multiple devices and/or multiple locations as may serve a particular implementation. Processing unit 1310 may be implemented by processor 108, controller 112, control circuit 204, and/or any other suitable processing and/or computing device or circuit.

Figure 14:
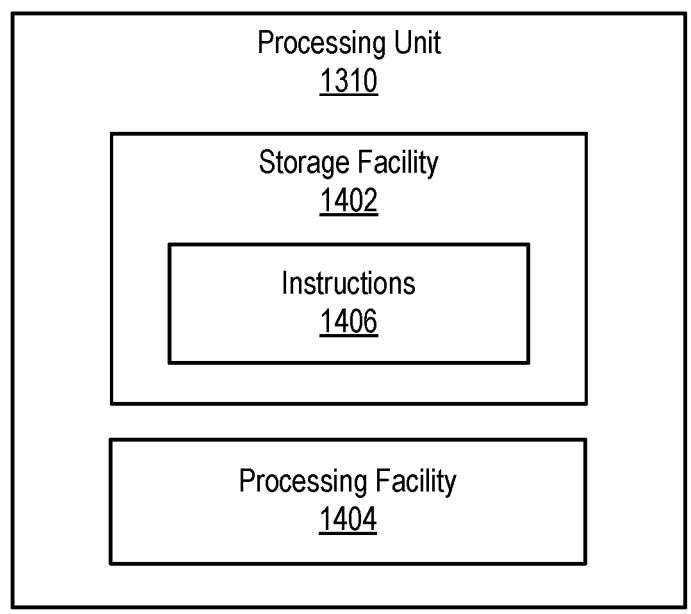
FIG. 14 illustrates an exemplary implementation of the processing unit of FIGS. 13A and 13B.

For example, FIG. 14 illustrates an exemplary implementation of processing unit 1310 in which processing unit 1310 includes a memory (storage facility) 1402 and a processor (processing facility) 1404 configured to be selectively and communicatively coupled to one another. In some examples, memory 1402 and processor 1404 may be distributed between multiple devices and/or multiple locations as may serve a particular implementation.

Memory 1402 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 1402 may maintain (e.g., store) executable data used by processor 1404 to perform one or more of the operations described herein. For example, memory 1402 may store instructions 1406 that may be executed by processor 1404 to perform any of the operations described herein. Instructions 1406 may be implemented by any suitable application, program (e.g., sound processing program), software, code, and/or other executable data instance. Memory 1402 may also maintain any data received, generated, managed, used, and/or transmitted by processor 1404.

Processor 1404 may be configured to perform (e.g., execute instructions 1406 stored in memory 1402 to perform) various operations described herein. For example, processor 1404 may be configured to perform any of the operations described herein as being performed by processing unit 1310.

FIGS. 15-20 illustrate embodiments of a wearable device 1500 that includes elements of the optical measurement systems described herein. In particular, the wearable devices 1500 include a plurality of modules 1502, similar to wearable modules 702 shown in FIG. 7, described herein. For example, each module 1502 includes a light source 704 and a plurality of detectors 706. Light source 704 may be implemented by or be similar to one or more light sources described herein (e.g., light source 110, light source 802, etc.). Each detector 706 may implement or be similar to one or more detectors or detector assemblies described herein (e.g., detector 104, detector 804, etc.) and may include a plurality of photodetectors. The wearable devices 1500 may each also include a controller (e.g., controller 112) and a processor (e.g., processor 108) and/or be communicatively connected to a controller and/or a processor. In general, wearable device 1500 may be implemented by any suitable headgear and/or clothing article configured to be worn by a user. The headgear and/or clothing article may include batteries, cables, and/or other peripherals for the components of the optical measurement systems described herein. In some examples, the headgear includes one or more modules 1502. Additionally or alternatively, modules 1502 are included in or implemented by modules 702.

Figure 15:
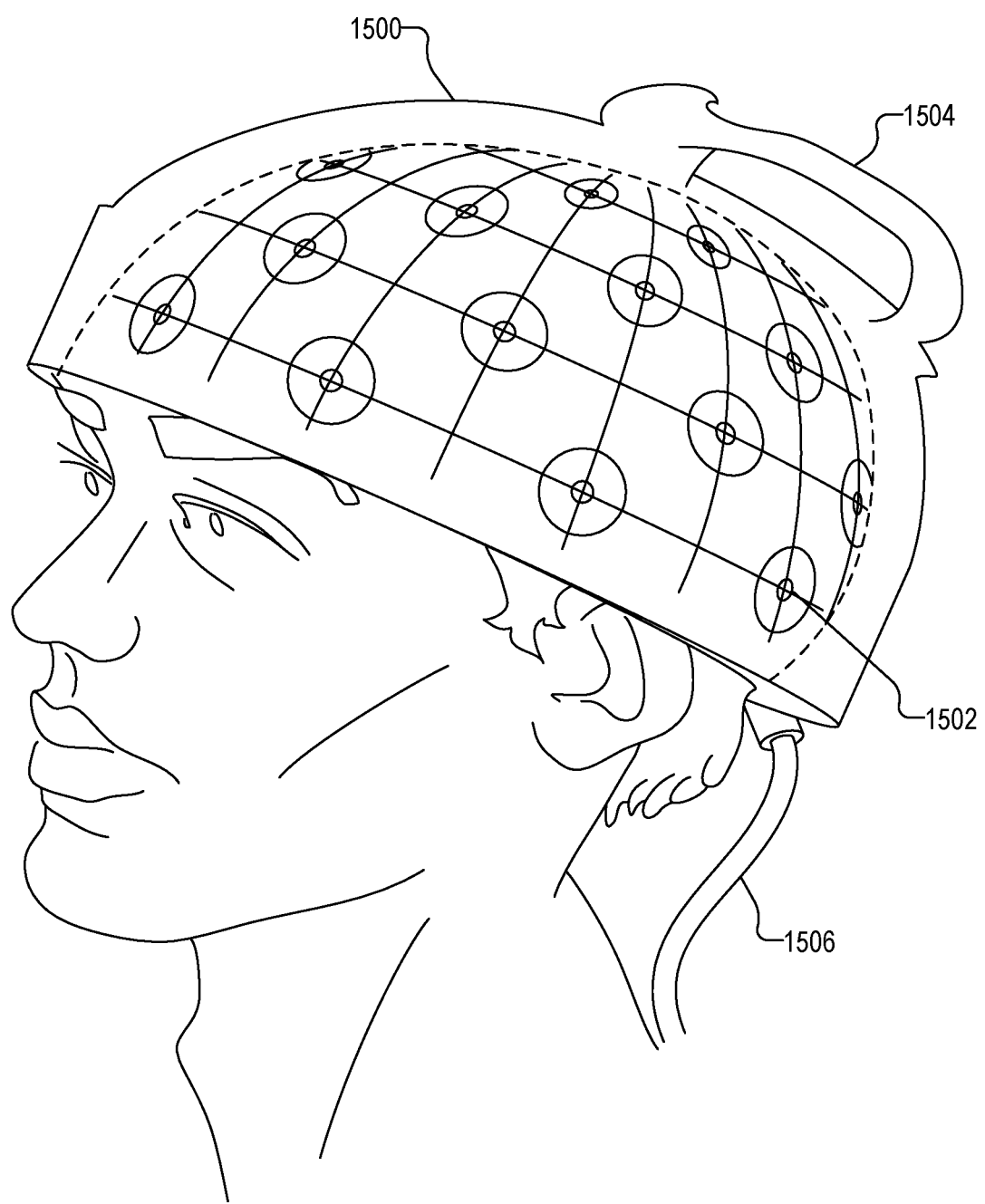
FIGS. 15-20 illustrate embodiments of a wearable device that includes elements of the optical detection systems described herein.
Figure 16:
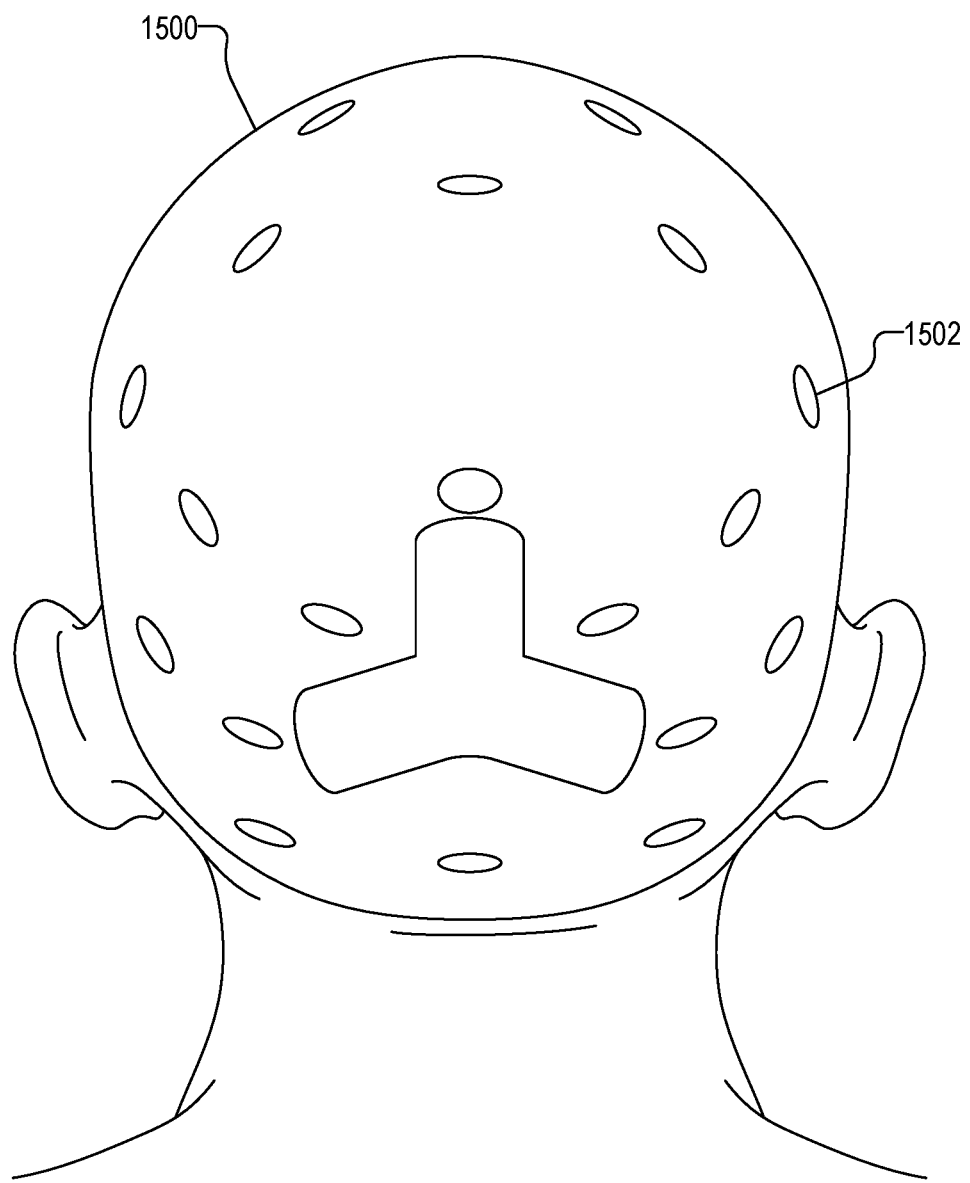
Figure 17:
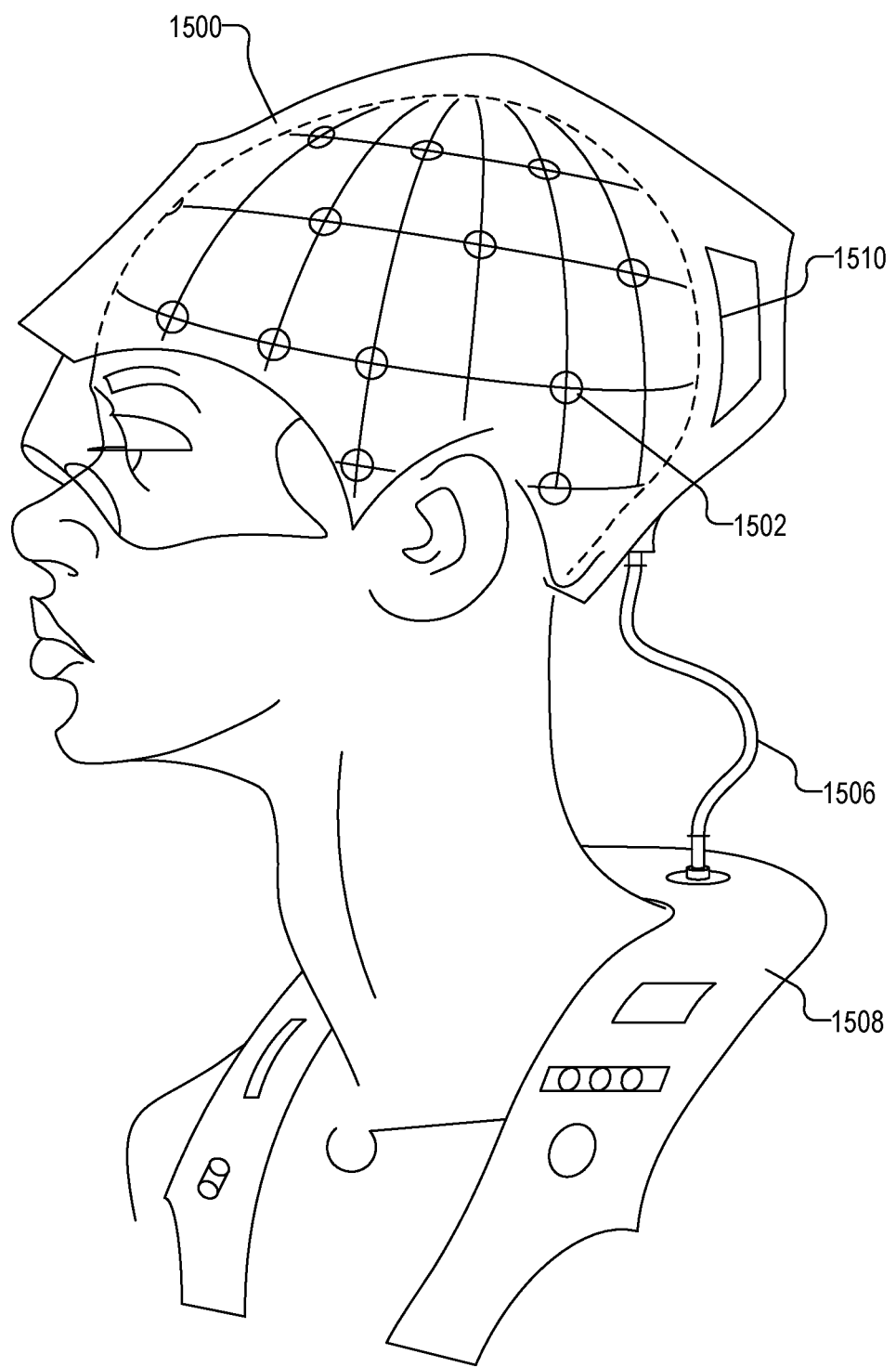

FIG. 15 illustrates an embodiment of a wearable device 1500 in the form of a helmet with a handle 1504. A cable 1506 extends from the wearable device 1500 for attachment to a battery or hub (with components such as a processor or the like). FIG. 16 illustrates another embodiment of a wearable device 1500 in the form of a helmet showing a back view. FIG. 17 illustrates a third embodiment of a wearable device 1500 in the form of a helmet with the cable 1506 leading to a wearable garment 1508 (such as a vest or partial vest) that can include a battery or a hub (e.g., processing unit 1310). Alternatively or additionally, the wearable device 1500 can include a crest 1510 or other protrusion for placement of the hub or battery.

Figure 18:
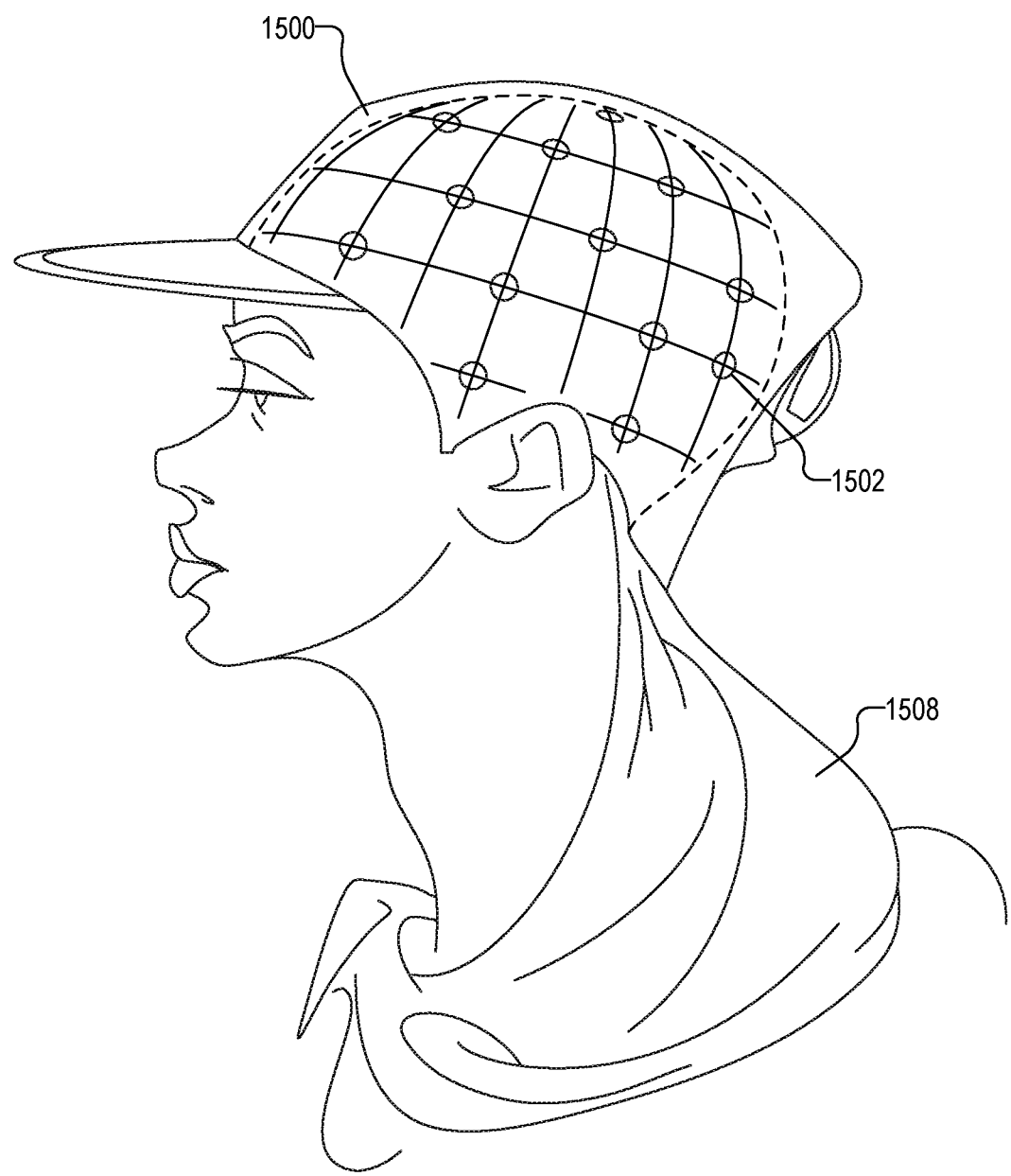
Figure 19:
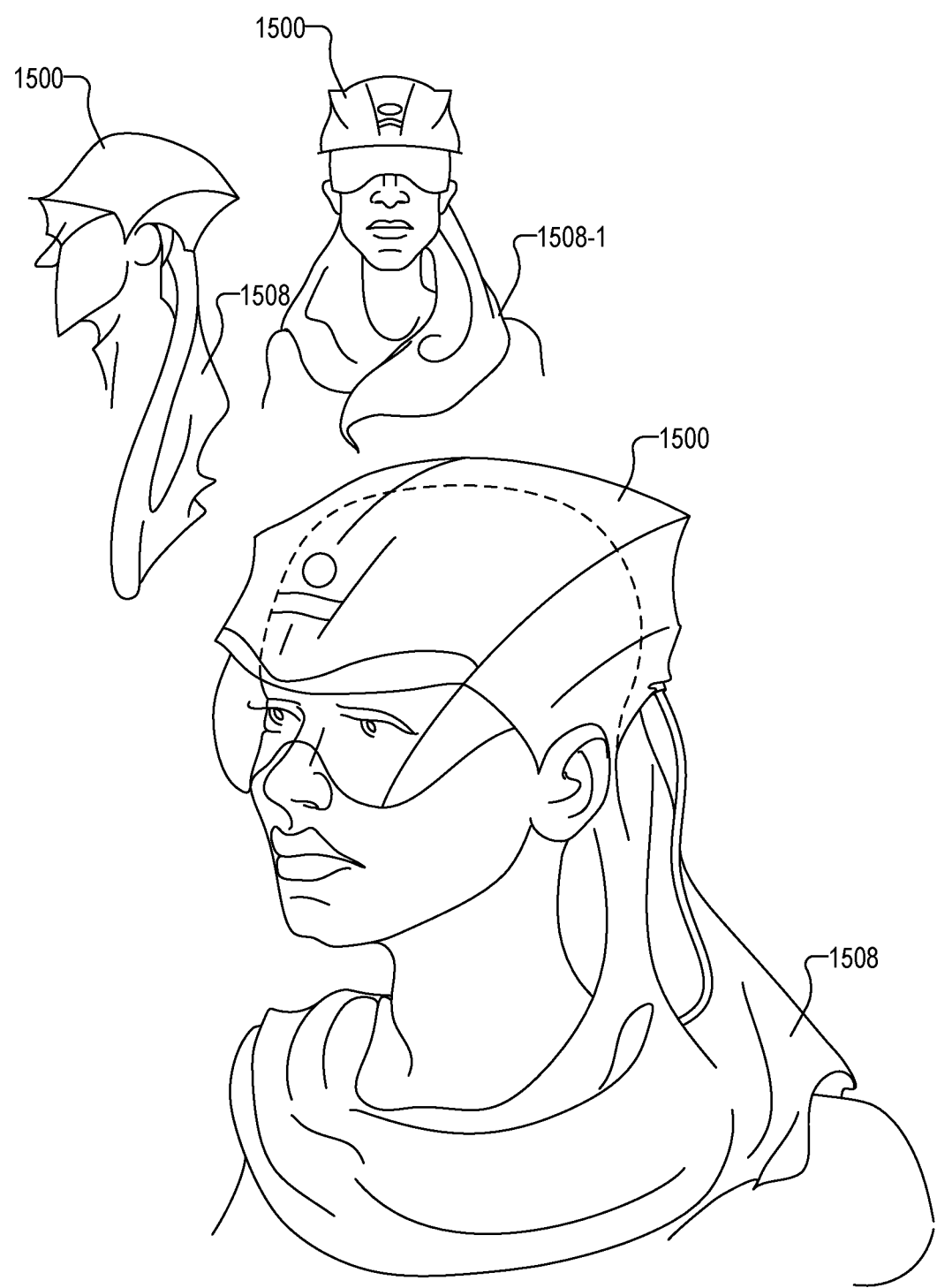
Figure 20:
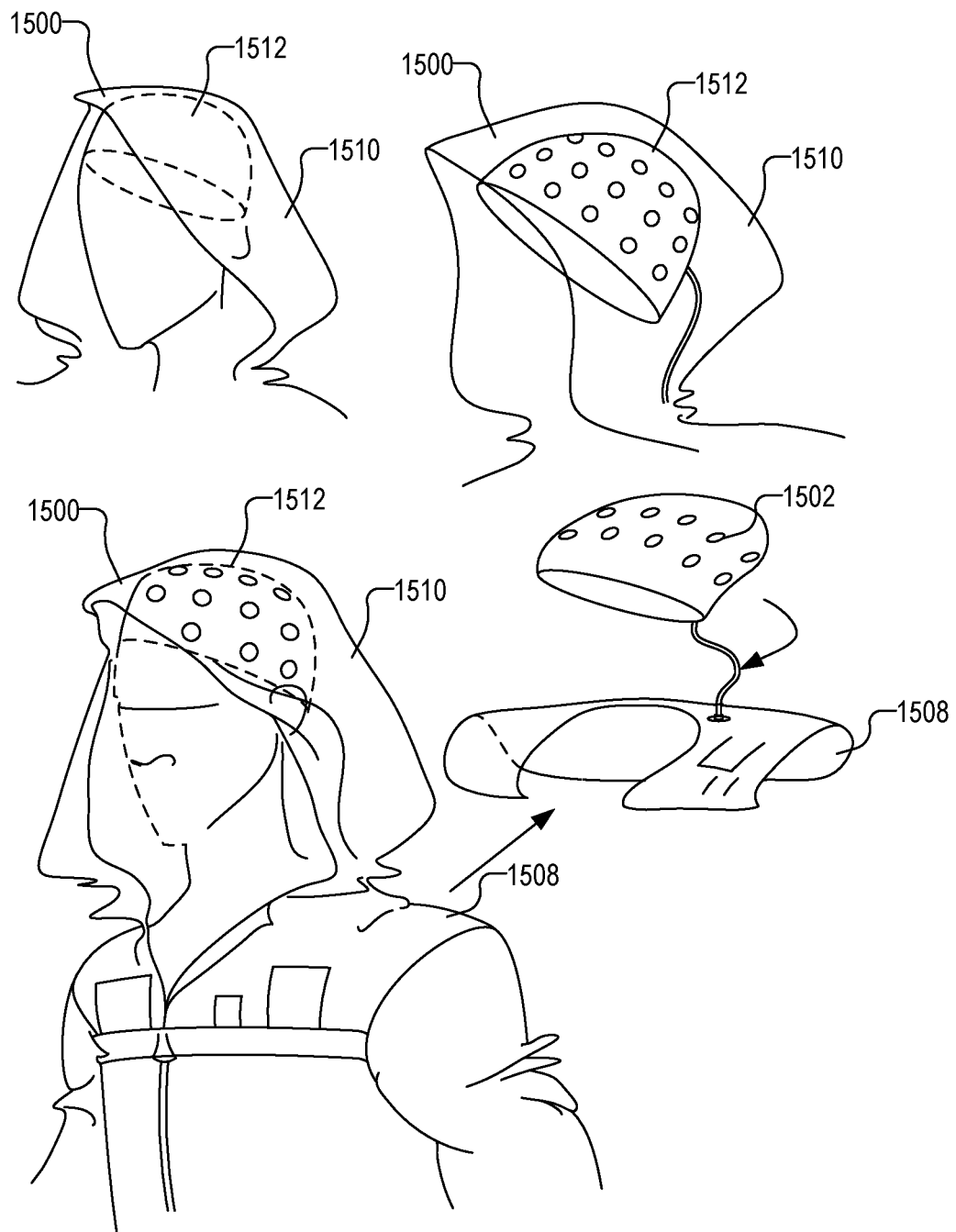

FIG. 18 illustrates another embodiment of a wearable device 1500 in the form of a cap with a wearable garment 1508 in the form of a scarf that may contain or conceal a cable, battery, and/or hub. FIG. 19 illustrates additional embodiments of a wearable device 1500 in the form of a helmet with a one-piece scarf 1508 or two-piece scarf 1508-1. FIG. 20 illustrates an embodiment of a wearable device 1500 that includes a hood 1510 and a beanie 1512 which contains the modules 1502, as well as a wearable garment 1508 that may contain a battery or hub.

Figure 21:
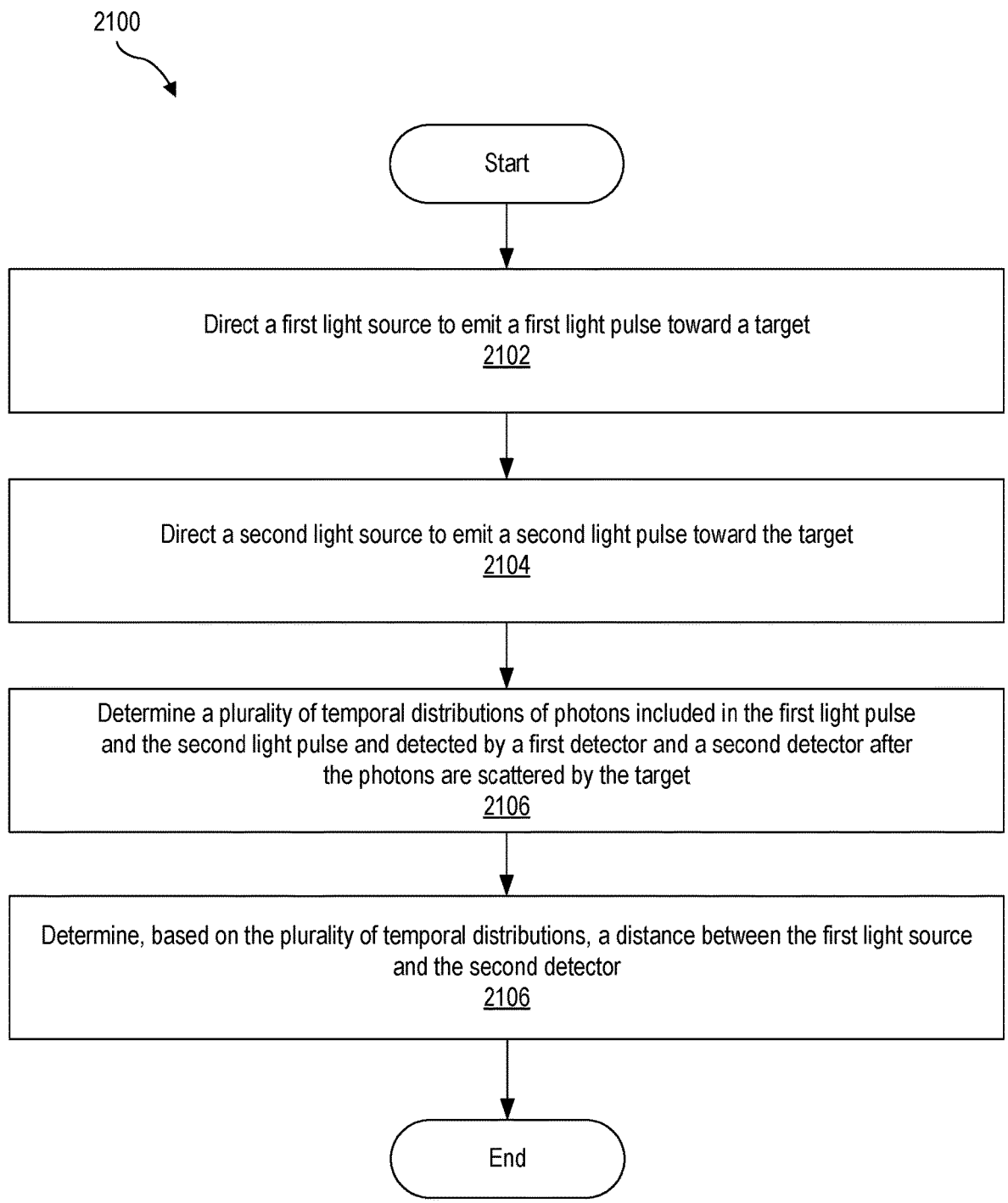
FIGS. 21 and 22 illustrate exemplary methods.

FIG. 21 illustrates an exemplary method 2100. While FIG. 21 illustrates exemplary operations according to one embodiment, other embodiments may omit, add to, reorder, and/or modify any of the operations shown in FIG. 21. One or more of the operations shown in FIG. 21 may be performed by any system described herein (e.g., optical measurement system 100, brain interface system 500, optical measurement system 700, or optical measurement system 800), any components included therein (e.g., wearable modules 702), and/or any implementation thereof.

In operation 2102, a first light source is directed to emit a first light pulse toward a target. Operation 2102 may be performed in any of the ways described herein.

In operation 2104, a plurality of temporal distributions of photons are determined. The photons are included in the first light pulse and the second light pulse and detected by a first detector and a second detector after the photons are scattered by the target. Operation 2104 may be performed in any of the ways described herein.

In operation 2106, the optical member directs the first light pulse and the second light pulse to a proximal end of a light guide included in the wearable module. Operation 2106 may be performed in any of the ways described herein.

In operation 2108, a distance between the first light source and the second detector is determined based on the plurality of temporal distributions. Operation 2108 may be performed in any of the ways described herein.

Figure 22:
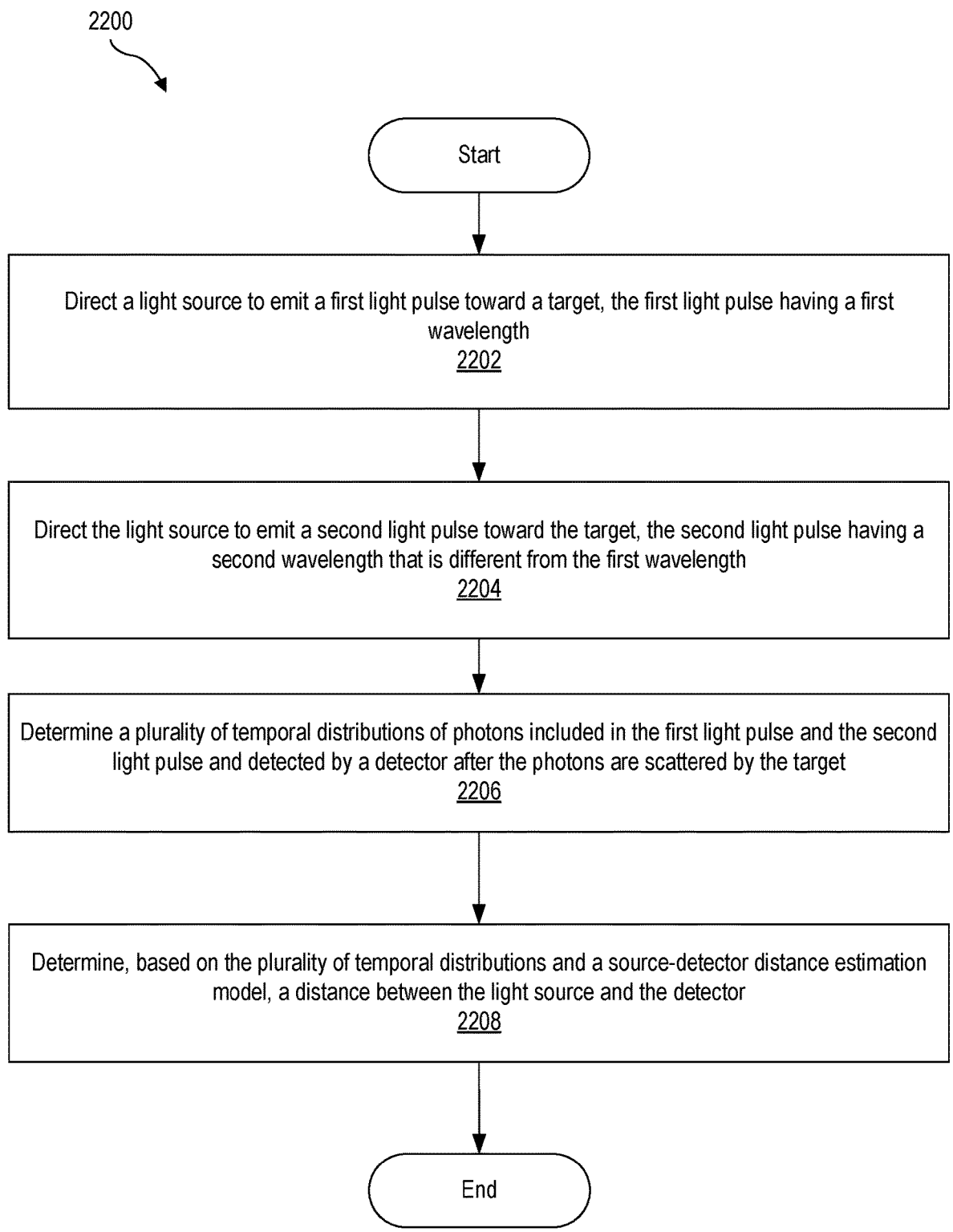

FIG. 22 illustrates an exemplary method 2200. While FIG. 22 illustrates exemplary operations according to one embodiment, other embodiments may omit, add to, reorder, and/or modify any of the operations shown in FIG. 22. One or more of the operations shown in FIG. 22 may be performed by any system described herein (e.g., optical measurement system 100, brain interface system 500, optical measurement system 700, or optical measurement system 800), any components included therein (e.g., wearable modules 702), and/or any implementation thereof.

In operation 2202, a light source is directed to emit a first light pulse toward a target, the first light pulse having a first wavelength. Operation 2202 may be performed in any of the ways described herein.

In operation 2204, the light source is directed to emit a second light pulse toward the target, the second light pulse having a second wavelength that is different from the first wavelength. Operation 2204 may be performed in any of the ways described herein.

In operation 2206, a plurality of temporal distributions of photons are determined, the photons being included in the first light pulse and the second light pulse and detected by a detector after the photons are scattered by the target. Operation 2206 may be performed in any of the ways described herein.

In operation 2208, a distance between the light source and the detector is determined based on the plurality of temporal distributions and a source-detector distance estimation model. Operation 2208 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 23:
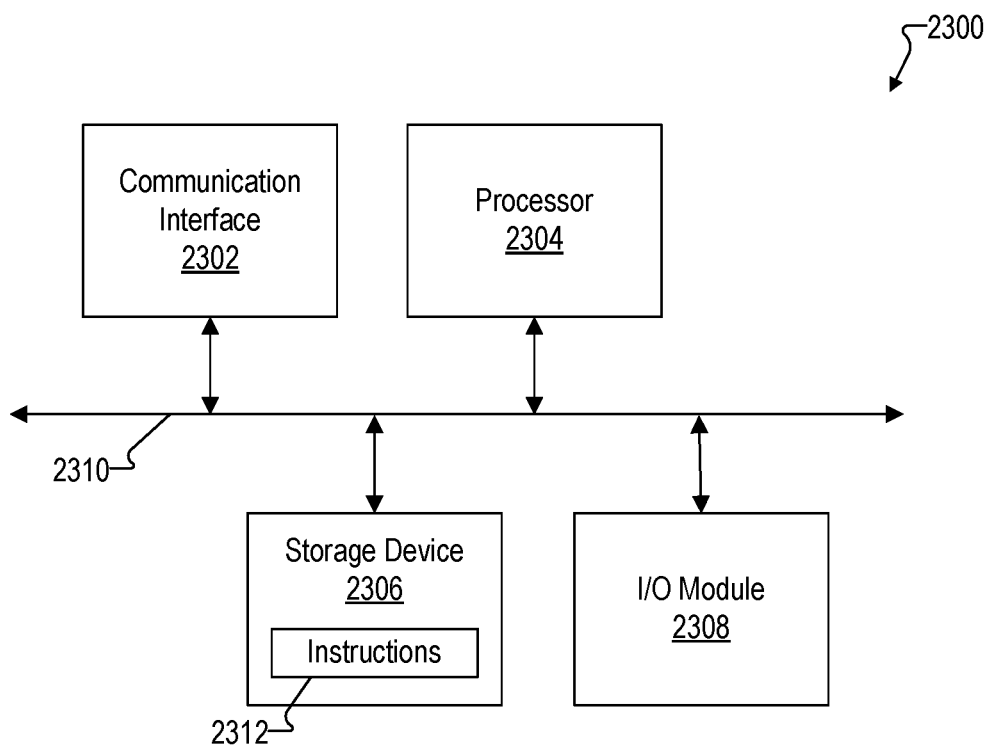
FIG. 23 illustrates an exemplary computing device.

FIG. 23 illustrates an exemplary computing device 2300 that may be specifically configured to perform one or more of the processes described herein. Any of the systems, units, computing devices, and/or other components described herein may be implemented by computing device 2300.

As shown in FIG. 23, computing device 2300 may include a communication interface 2302, a processor 2304, a storage device 2306, and an input/output ("I/O") module 2308 communicatively connected one to another via a communication infrastructure 2310. While an exemplary computing device 2300 is shown in FIG. 23, the components illustrated in FIG. 23 are not intended to be limiting. Additional or alternative components may be used in other embodiments. Components of computing device 2300 shown in FIG. 23 will now be described in additional detail.

Communication interface 2302 may be configured to communicate with one or more computing devices. Examples of communication interface 2302 include, without limitation, a wired network interface (such as a network interface card), a wireless network interface (such as a wireless network interface card), a modem, an audio/video connection, and any other suitable interface.

Processor 2304 generally represents any type or form of processing unit capable of processing data and/or interpreting, executing, and/or directing execution of one or more of the instructions, processes, and/or operations described herein. Processor 2304 may perform operations by executing computer-executable instructions 2312 (e.g., an application, software, code, and/or other executable data instance) stored in storage device 2306.

Storage device 2306 may include one or more data storage media, devices, or configurations and may employ any type, form, and combination of data storage media and/or device. For example, storage device 2306 may include, but is not limited to, any combination of the non-volatile media and/or volatile media described herein. Electronic data, including data described herein, may be temporarily and/or permanently stored in storage device 2306. For example, data representative of computer-executable instructions 2312 configured to direct processor 2304 to perform any of the operations described herein may be stored within storage device 2306. In some examples, data may be arranged in one or more databases residing within storage device 2306.

I/O module 2308 may include one or more I/O modules configured to receive user input and provide user output. I/O module 2308 may include any hardware, firmware, software, or combination thereof supportive of input and output capabilities. For example, I/O module 2308 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 2308 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 2308 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An optical measurement system comprising:
    a first light source configured to emit a first light pulse toward a target;
    a second light source configured to emit a second light pulse toward the target;
    a first detector;
    a second detector; and
    a processing unit configured to:
        determine a plurality of temporal distributions of photons included in the first light pulse and the second light pulse and detected by the first detector and the second detector after the photons are scattered by the target, and
        determine, based on the plurality of temporal distributions, a source-detector distance between the first light source and the second detector.

2. The optical measurement system of claim 1, wherein the processing unit is further configured to determine, based on the plurality of temporal distributions, a source-detector distance between the second light source and the first detector.

3. The optical measurement system of claim 1, wherein the plurality of temporal distributions comprises:
    a first temporal distribution of a first set of photons included in the first light pulse and detected by the first detector after the first set of photons are scattered by the target in a first region;
    a second temporal distribution of a second set of photons included in the first light pulse and detected by the second detector after the second set of photons are scattered by the target in the first region and a third region located between the first region and a second region;
    a third temporal distribution of a third set of photons included in the second light pulse and detected by the second detector after the third set of photons are scattered by the target in the second region; and
    a fourth temporal distribution of a fourth set of photons included in the second light pulse and detected by the first detector after the fourth set of photons are scattered by the target in the second region and the third region.

4. The optical measurement system of claim 3, wherein:
    the first detector is separated from the first light source by a first source-detector distance;
    the second detector is separated from the second light source by a second source-detector distance; and
    the processing unit is configured to determine the source-detector distance between the first light source and the second detector further based on the first source-detector distance and the second source-detector distance.

5. The optical measurement system of claim 4, wherein the first source-detector distance and the second source-detector distance are fixed.

6. The optical measurement system of claim 4, wherein the processing unit is configured to determine the source-detector distance between the first light source and the second detector by:
    determining, based on the first temporal distribution and the first source-detector distance, a first reduced scattering coefficient $\mu's1$ of the target within the first region;
    determining, based on the third temporal distribution and the second source-detector distance, a second reduced scattering coefficient $\mu's2$ of the target within the second region; and
    determining, based on the second temporal distribution and the fourth temporal distribution, a third reduced scattering coefficient $\mu's3$ of the target within the third region and a distance between the first detector and the second detector.

7. The optical measurement system of claim 1, wherein:
    the first light source is further configured to emit a third light pulse toward the target;
    the second light source is further configured to emit a fourth light pulse toward the target;
    the first light pulse and the second light pulse have a first wavelength;
    the third light pulse and the fourth light pulse have a second wavelength different from the first wavelength; and
    the processing unit is further configured to:
        determine a plurality of additional temporal distributions of additional photons included in the third light pulse and the fourth light pulse and detected by the first detector and the second detector after the additional photons are scattered by the target, and
        determine, based on the plurality of additional temporal distributions, the source-detector distance between the first light source and the second detector.

8. The optical measurement system of claim 1, wherein the processing unit is further configured to:
    direct the first light source to emit the first light pulse; and
    direct the second light source to emit the second light pulse after the first light source emits the first light pulse.

9. The optical measurement system of claim 1, wherein the first detector and the second detector are positioned inline with the first light source and the second light source.

10. The optical measurement system of claim 1, wherein the first detector and the second detector each comprises a plurality of single-photon avalanche diode (SPAD) circuits.

11. The optical measurement system of claim 1, further comprising:
    a first wearable module comprising a first housing and the first light source and the first detector housed within the first housing; and
    a second wearable module comprising a second housing and the second light source and the second detector housed within the second housing.

12. The optical measurement system of claim 11, wherein the second wearable module is movable relative to the first wearable module.

13. The optical measurement system of claim 11, wherein the second wearable module is positioned adjacent to the first wearable module.

14. The optical measurement system of claim 11, wherein the first wearable module and the second wearable module are included in a head-mountable component configured to be worn on a head of a user.

15. The optical measurement system of claim 11, wherein the processing unit is housed in one or more of the first housing or the second housing.

16. The optical measurement system of claim 11, further comprising a third housing separate from the first housing and the second housing,
wherein the processing unit is housed in the third housing and communicatively coupled with the first detector and the second detector by way of one or more wired or wireless communication links.

17. The optical measurement system of claim 16, wherein the third housing is wearable by a user.

18. The optical measurement system of claim 1, wherein the target comprises a brain of a user.

19. A method comprising:
directing, by an optical measurement system, a first light source to emit a first light pulse toward a target;
directing, by the optical measurement system, a second light source to emit a second light pulse toward the target;
determining, by the optical measurement system, a plurality of temporal distributions of photons included in the first light pulse and the second light pulse and detected by a first detector and a second detector after the photons are scattered by the target; and
determining, by the optical measurement system based on the plurality of temporal distributions, a source-detector distance between the first light source and the second detector.

20. The method of claim 19, further comprising determining, by the optical measurement system based on the plurality of temporal distributions, a source-detector distance between the second light source and the first detector.

21. The method of claim 19, wherein the plurality of temporal distributions comprises:
a first temporal distribution of a first set of photons included in the first light pulse and detected by the first detector after the first set of photons are scattered by the target in a first region;
a second temporal distribution of a second set of photons included in the first light pulse and detected by the second detector after the second set of photons are scattered by the target in the first region and a third region located between the first region and a second region;
a third temporal distribution of a third set of photons included in the second light pulse and detected by the second detector after the third set of photons are scattered by the target in the second region; and
a fourth temporal distribution of a fourth set of photons included in the second light pulse and detected by the first detector after the fourth set of photons are scattered by the target in the second region and the third region.

22. The method of claim 21, wherein:
the first detector is separated from the first light source by a first source-detector distance;
the second detector is separated from the second light source by a second source-detector distance; and
the source-detector distance between the first light source and the second detector is determined further based on the first source-detector distance and the second source-detector distance.

23. The method of claim 22, wherein the first source-detector distance and the second source-detector distance are fixed.

24. The method of claim 22, wherein the determining of the source-detector distance between the first light source and the second detector comprises:
determining, based on the first temporal distribution and the first source-detector distance, a first reduced scattering coefficient $\mu's1$ of the target within the first region;
determining, based on the third temporal distribution and the second source-detector distance, a second reduced scattering coefficient $\mu's2$ of the target within the second region; and
determining, based on the second temporal distribution and the fourth temporal distribution, a third reduced scattering coefficient $\mu's3$ of the target within the third region and a distance between the first detector and the second detector.

25. The method of claim 19, further comprising:
directing, by the optical measurement system, the first light source to emit a third light pulse toward the target;
directing, by the optical measurement system, the second light source to emit a fourth light pulse toward the target;
determining, by the optical measurement system, a plurality of additional temporal distributions of additional photons included in the third light pulse and the fourth light pulse and detected by the first detector and the second detector after the additional photons are scattered by the target; and
determining, by the optical measurement system based on the plurality of additional temporal distributions, the source-detector distance between the first light source and the second detector,
wherein the first light pulse and the second light pulse have a first wavelength and the third light pulse and the fourth light pulse have a second wavelength different from the first wavelength.

26. The method of claim 19, wherein the second light pulse is emitted after the first light pulse.

27. The method of claim 19, wherein the target comprises a brain of a user.

* * * * *